US010703708B2

(12) United States Patent
Guerard et al.

(10) Patent No.: US 10,703,708 B2
(45) Date of Patent: Jul. 7, 2020

(54) METHOD FOR SYNTHESIZING IODO- OR ASTATOARENES USING DIARYLIODONIUM SALTS

(71) Applicants: INSTITUT NATIONAL DE LA SANTE ET DE LA RECHERCHE MEDICALE (INSERM), Paris (FR); CENTRE NATIONAL DE LA RECHERCHE SCIENTIFIQUE, Paris (FR); UNIVERSITE DE NANTES, Nantes (FR); UNIVERSITE D'ANGERS, Angers (FR); THE GOVERNMENT OF THE UNITED STATES OF AMERICA, AS REPRESENTED BY THE SECRETARY, DEPARTMENT OF HEALTH AND HUMAN SERVICES, Rockville, MD (US)

(72) Inventors: François Guerard, Nantes (FR); Jean-François Gestin, Nantes (FR); Martin W. Brechbiel, Bethesda, MD (US); Yong-Sok Lee, Bethesda, MD (US)

(73) Assignees: INSTITUT NATIONAL DE LA SANTE ET DE LA RECHERCHE MEDICALE (INSERM), Paris (FR); CENTRE NATIONAL DE LA RECHERCHE SCIENTIFIQUE, Paris (FR); UNIVERSITE DE NANTES, Nantes (FR); UNIVERSITE D'ANGERS, Angers (FR); THE GOVERNMENT OF THE UNITED STATES OF AMERICA, AS REPRESENTED BY THE SECRETARY, DEPARTMENT OF HEALTH AND HUMAN SERVICES, Rockville, MD (US)

( * ) Notice: Subject to any disclaimer, the term of this patent is extended or adjusted under 35 U.S.C. 154(b) by 0 days.

(21) Appl. No.: 15/777,828

(22) PCT Filed: Nov. 24, 2016

(86) PCT No.: PCT/EP2016/078729
§ 371 (c)(1),
(2) Date: May 21, 2018

(87) PCT Pub. No.: WO2017/089492
PCT Pub. Date: Jun. 1, 2017

(65) Prior Publication Data
US 2019/0023646 A1 Jan. 24, 2019

(30) Foreign Application Priority Data

Nov. 24, 2015 (EP) .................... 15306862

(51) Int. Cl.
C07C 201/12 (2006.01)
C07C 67/307 (2006.01)
C07C 41/18 (2006.01)
C07B 59/00 (2006.01)
C07C 247/10 (2006.01)
C07C 247/16 (2006.01)
C07D 207/46 (2006.01)
C07C 253/30 (2006.01)
C07C 25/24 (2006.01)
C07C 17/361 (2006.01)
C07C 43/225 (2006.01)
(Continued)

(52) U.S. Cl.
CPC .......... C07C 201/12 (2013.01); C07B 59/001 (2013.01); C07B 59/002 (2013.01); C07B 59/008 (2013.01); C07C 17/361 (2013.01); C07C 25/24 (2013.01); C07C 29/10 (2013.01); C07C 29/58 (2013.01); C07C 29/62 (2013.01); C07C 33/46 (2013.01); C07C 41/18 (2013.01); C07C 43/225 (2013.01); C07C 67/307 (2013.01); C07C 247/10 (2013.01); C07C 247/16 (2013.01); C07C 253/30 (2013.01); C07D 207/46 (2013.01); C07B 2200/05 (2013.01)

(58) Field of Classification Search
CPC ....................................... C07C 25/24
See application file for complete search history.

(56) References Cited

U.S. PATENT DOCUMENTS 3,863,010 A 1/1975 Lang, Jr. et al.

FOREIGN PATENT DOCUMENTS

WO 98/18499 A1 5/1998
WO 2005/021472 A2 3/2005
(Continued)

OTHER PUBLICATIONS

Hu et al. "An Alternative to the Sandmeyer Approach to Aryl Iodides" Chem. Eur. J. 2015, vol. 21, No. 17, pp. 6934-6938.*
(Continued)

Primary Examiner — Joseph R Kosack
(74) Attorney, Agent, or Firm — W&C IP

(57) ABSTRACT

The present invention concerns a method of synthesizing a iodo- or astatoarene comprising the reaction of a diaryliodonium compound with a iodide or astatide salt, respectively. The invention also relates to said iodo- or astatoarene and diaryliodonium compound as such. The invention also concerns a method of synthesizing a iodo- or astatolabelled biomolecule and/or vector using said iodo- or astatoarene.

14 Claims, 1 Drawing Sheet

(51) Int. Cl.
  *C07C 29/62*   (2006.01)
  *C07C 29/10*   (2006.01)
  *C07C 29/58*   (2006.01)
  *C07C 33/46*   (2006.01)

(56) References Cited

FOREIGN PATENT DOCUMENTS

WO    2005/097713 A1    10/2005
WO    2011/095517 A1    8/2011

OTHER PUBLICATIONS

Hu et al. "An Alternative to the Sandmeyer Approach to Aryl Iodides" Chem. Eur. J. 2015, Supporting Information pp. 1-59.*
Spetz et al. "Biodistribution and Dosimetry of Free 211At, 125I- and 131I—in Rats" Cancer Biotherapy and Radiopharmaceuticals, 2013, vol. 28, No. 9, pp. 657-664.*
Gotteland J-P et al: "Design and synthesis of new potential photoaffinity labels for mammalian squalene epoxidase", Bioorganic & Medicinal Chemistry Letters, Pergamon, Amsterdam, NL, vol. 7, No. 9, May 6, 1997, pp. 1153-1156.
Lee J et al: "N-[4-(Methylsulfonylamino)benzyl]thiourea analogues as vanilloid receptor antagonists: analysis of structure-activity relationships for the 'C-Region'", Bioorganic & Medicinal Chemistry, Pergamon, GB, vol. 12, No. 2, Jan. 1, 2004, pp. 371-385.
Lavastre O et al: "Selective and Efficient Access to Ortho, Meta and Para Ring-substituted Phenylacetylene Derivatives R-[C Identical C-C6H4] x-Y (Y : H, NO2, CN, I, NH2)", Tetrahedron, Elsevier Science Publishers, Amsterdam, NL, vol. 53, No. 22, Jun. 2, 1997, pp. 7595-7604.

* cited by examiner

METHOD FOR SYNTHESIZING IODO- OR ASTATOARENES USING DIARYLIODONIUM SALTS

The present invention concerns a method of synthesizing a iodo- or astatoarene comprising the reaction of a diaryliodonium compound with a iodide or astatide salt, respectively. The invention also relates to said iodo- or astatoarene and diaryliodonium compound as such. The invention also concerns a method of synthesizing a iodo- or astatolabelled biomolecule and/or vector using said iodo- or astatoarene.

Aryliodonium salts have become increasingly popular in the last decades for arylation of nucleophiles thanks to their low toxicity, the high regioselectivity they allow and the mild reaction conditions they require compared to conventional methods. Halogens were amongst the first nucleophiles to be closely investigated for the nucleophilic aromatic substitution of aryliodonium salts more than 50 years ago. Yet, this is only recently that applications related to halogenation with these precursors have been developed, especially in radiochemistry with the radiolabelling of arenes with the $\beta^+$-emitter fluorine-18 for positron emitted tomography (PET).

In contrast to $^{18}F$, the other radiohalogens have received limited attention for reaction with iodonium salts. For instance, no report exists as to the reactivity of radioactive bromide, iodide and astatide.

Many of the radioiodinated and astatinated compounds of interest in nuclear medicine are aromatic derivatives since non-aromatic compounds often exhibit poor stability due to the weakness of the C—I and C—At bonds. These aromatic compounds are generally obtained by conventional methods such as nucleophilic substitution by halogen exchange, electrophilic substitution by halodemetallation, for example the usual astatodestannylation method, or by direct substitution.

However, these reactions are often associated with issues related to low radiochemical yields (RCYs), low specific activity, or concerns about the toxicity of the precursors and side products when considering human use.

Moreover, in the particular case of astatination of aromatic compounds, the electrophilic substitution of arylstannane is often the preferred method because of the high yields generally obtained in smooth conditions. However, with astatine which can exist in several oxidation states (−I, +I, +III, +V and +VII), obtaining pure At(+I) at ultra-trace concentration is difficult to control, and mixtures of At(+I) and At(+III) species are difficult to avoid. Additionally, it was shown that the +I oxidation state was not stable over time due to the radiations arising from the decay of astatine to which it is exposed in solution, leading to changes in its oxidation state.

There is thus a need to provide new methods of synthesizing a iodo- or astatoarene, more particularly a radioiodo- or radioastatoarene. There is also a need to provide radiolabelled biomolecules and/or vector with radioactive isotopes of iodine or astatine.

One aim of the present invention is to provide a method of synthesizing a iodo- or astatoarene, more particularly with high and consistent yields.

One aim of the invention is to provide a method of synthesizing a iodo- or astatoarene which is easy to perform, in particular with an efficient, fast and low-cost purification step.

Another aim of the invention is to provide a method of synthesizing a iodo- or astatoarene which is less toxic than the iodo- or astatodestannylation method, more particularly which avoids the use of intermediate compounds comprising tin and leading to toxic side products.

Another particular aim of the present invention is to provide a method of synthesizing an astatoarene that involves the use of astatine in the (−I) oxidation state.

One aim of the invention is also to provide radiolabelled biomolecules and vectors, using said iodo- or astatoarenes.

The present invention thus relates to a method of synthesizing a iodo- or astatoarene comprising the reaction of a diaryliodonium compound with a iodide or astatide salt, respectively.

Surprisingly, the inventors found that iodo- or astatoarene compounds can be obtained thanks to the reaction of a diaryliodonium compound with a iodide(−I) or astatide(−I) salt, in particular with high efficiency with astatide(−I). The reaction of a diaryliodonium compound with a iodide or astatide salt leads to good yields of iodo- or astatoarene and is less toxic than the halodemetallation method, more particularly less toxic than the iododestannylation and the astatodestannylation methods.

The inventors also found a purification technique of iodo- or astatoarene compounds. HPLC (High Performance Liquid Chromatogaphy) is usually used to separate the iodo- or astatoarene from the reagents and side-products, for example before the coupling with a biomolecule. Performing a HPLC takes time and leads to a decrease of the radiochemical yield (in particular with $^{211}At$ which half-life is about 7.214 h). Given the extremely low amount of astatinated species involved, such HPLC purification also generally leads to important losses by adsorption within the chromatographic system (up to 80% of the astatinated product of interest). The extraction by a solvent such as diethylether of the iodo- or astatoarene found by the inventors is easier, faster and low-cost compared to HPLC. The purification step is thus improved and adapted to an industrial scale.

Even more striking, the inventors found that astatide presents a unexpectedly higher reactivity than iodide in this context. This is surprising because compared to iodide, the chemical behavior of astatide is often similar, whereas the chemical behavior of higher oxidation states of astatine is not well understood and can differ significantly from the trends observed with the other halogens.

To invoke the higher nucleophilicity of the astatide anion alone is not sufficient to explain the sharp increase in reactivity obtained with astatide as compared to iodide in the context of the invention. To explain this difference of reactivity and without being bound by a theory, the reaction intermediate, iodonium iodide, may be stabilized in the form of a dimer or a higher cluster which requires more energy for dissociation, whereas the iodonium astatide forms more easily the monomeric form due to the formation of a contact ion pair favored by greater polarisability of the heaviest halogenide.

The method according to the invention thus leads to iodo- or astatoarene compounds and more particularly to radioiodo- or radioastatoarene compounds which can be useful in nuclear medicine. In particular, radioiodo- or radioastatoarene compounds according to the invention may be conjugated to biomolecules and/or vectors and thus used in the treatment and/or localisation of tumors.

Definitions

The term "$(C_1-C_6)$alkyl" means a saturated aliphatic hydrocarbon group which may be straight or branched having 1 to 6 carbon atoms in the chain. "Branched" means that one or lower alkyl groups such as methyl, ethyl or propyl are attached to a linear alkyl chain. «Lower alkyl» means 1 to 4 carbon atoms in the chain which may be straight or branched. Preferred alkyl groups are methyl, ethyl, propyl and isopropyl.

By "$(C_2-C_6)$alkenyl" is meant an unsaturated alkyl, comprising at least one double bond between two carbon atoms and comprising from 2 to 6 carbon atoms, preferably from 2 to 4 carbon atoms.

By "$(C_2-C_6)$alkynyl" is meant an unsaturated alkyl, comprising at least one triple bond between two carbon atoms and comprising from 2 to 6 carbon atoms, preferably from 2 to 4 carbon atoms.

The term "$(C_6-C_{10})$aryl" refers to an aromatic monocyclic, bicyclic, or tricyclic hydrocarbon ring system, wherein any ring atom capable of substitution may be substituted by a substituent. Examples of aryl moieties include, but are not limited to, phenyl and naphthyl, preferably phenyl.

The term "heteroaryl" refers to a 5- to 10-membered aromatic monocyclic or bicyclic group containing from 1 to 4 heteroatom(s) selected from O, S or N, preferably S, wherein any ring atom capable of substitution may be substituted by a substituent. Examples of heteroaryl moieties include, but are not limited to thiophene or tetrazine such as 4-methyl-[1,2,4,5]-tetrazine or 3-methyl-[1,2,4,5]-tetrazine.

The term "halogen" (or "Hal") refers to the atoms of the group 17 of the periodic table (halogens) and includes fluorine, chlorine, bromine, iodine and astatine atoms, preferably chlorine, bromine, iodine and astatine atoms. The term "heavy halogen" refers to iodine and astatine atoms.

The term "cyclooctynyl" may refer to a compound having the following formula (i), wherein R is $Ar_1$ or $Ar_2$ as defined below:

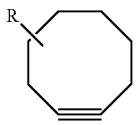

(i)

The term "norbornenyl" may refer to a compound having the following formula (ii), wherein R is $Ar_1$ or $Ar_2$, as defined below:

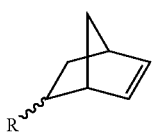

(ii)

The term "cyclopropenyl" may refer to compounds having the following formula (iii), wherein R is $Ar_1$ or $Ar_2$ and R' being H or $(C_1-C_6)$alkyl:

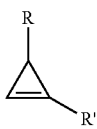

(iii)

The term "bicyclononynyl" may refer to a compound having the following formula (iv), wherein R is $Ar_1$ or $Ar_2$:

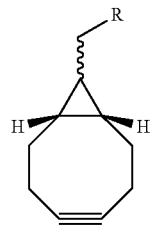

(iv)

The term "trans-cyclooctenyl" may refer to compounds having one of the following formulae (v) or (vi), wherein R is $Ar_1$ or $Ar_2$:

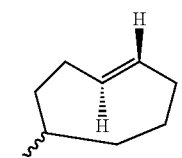

(v)

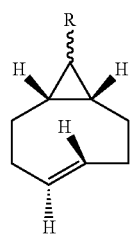

(vi)

The term "vector" refers to a molecule being able to recognize a biological target tissue (depending on the pathology to be treated or detected).

The term "vector" may also refer to organic compounds binding cells or organic compounds transported by transporters expressed by cells (e.g., but not limited to, glucose, amino-acids, biogenic amines), peptides binding specific receptors (e.g. but not limited to somatostatine, cholecystokinine, neurotensine receptors, substance P), haptens and drugs.

The term "vector" may also refer to a nanocarrier compound able to recognize the target cells such as a nanocapsule, a liposome, a dendrimer or a carbon nanotube. These nanocarriers may be linked if necessary to tumor specific ligands.

By "biomolecules", it is understood an antibody or fragments thereof or any antibody construct (like minibodies, diabodies etc . . . resulting from antibody engineering) as well as recombinant proteins or synthetic peptides selected to bind target cells (e.g., but not limited to, affibodies or affitins).

The expression "functional groups being able to bind a vector and/or a biomolecule" refers to a chemical group which is reactive towards the chemical functions of a vector and/or a biomolecule and thus allows the formation of a stable chemical bond between the vector and/or the biomolecule and the synthon (which is the iodo- or astatoarene according to the invention, preferably of formula (I) or (I-1)).

Method of Synthesizing a iodo- or astatoarene

Reaction of a Diaryliodonium Compound of Formula (II) or (II-1) with a Iodide or Astatide Salt The invention relates to a method of synthesizing a iodo- or astatoarene comprising the reaction of a diaryliodonium compound with a iodide or astatide salt, respectively, wherein the diaryliodonium compound is of formula (II):

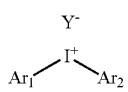

(II)

wherein:
Ar$_1$ and Ar$_2$, independently of each other, are chosen from: (C$_6$-C$_{10}$)aryl and heteroaryl groups, said aryl and heteroaryl groups being substituted with one or several substituents selected from: (C$_1$-C$_6$)alkyl, (C$_2$-C$_6$)alkynyl, optionally substituted heteroaryl, halogen, NO$_2$, CN, N$_3$, CF$_3$, —ORa, —COORb, —C(O)Ra, —N═C═O, —N═C═S, —N(Ra)COORb, —(C$_1$-C$_6$)alkylene-N(Ra)—C(O)—Rb, —(C$_1$-C$_6$)alkylene-N(Ra)—C(O)—(C$_1$-C$_6$)alkylene-Rb, —(C$_1$-C$_6$)alkylene-N(Ra)—C(O)—(C$_1$-C$_6$)alkylene-C(O)O—Rb and maleimidyl,
said (C$_1$-C$_6$)alkyl group being optionally substituted with one or several substituents selected from N$_3$, OH, OCH$_3$, CF$_3$, —O—CH$_2$—O—(C$_1$-C$_6$)alkyl and O—(C$_1$-C$_6$)alkenyl;
Ra being H or (C$_1$-C$_6$)alkyl;
Rb being chosen from the group consisting of: H, (C$_1$-C$_6$)alkyl and functional groups being able to bind a vector and/or a biomolecule; and
Y is a monovalent anion, in particular chosen from: CF$_3$COO, TsO, MsO (mesylate), NsO (nosylate), TfO, NO$_3$, Br, Cl, SO$_4$ and BF$_4$.

The invention also relates to a method of synthesizing a iodo- or astatoarene comprising the reaction of a diaryliodonium compound with a iodide or astatide salt, respectively, wherein the diaryliodonium compound is of formula (II):

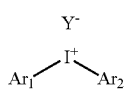

(II)

wherein:
Ar$_1$ and Ar$_2$, independently of each other, are chosen from: (C$_6$-C$_{10}$)aryl and heteroaryl groups, said aryl and heteroaryl groups being substituted with one or several substituents selected from: (C$_1$-C$_6$)alkyl, (C$_2$-C$_6$)alkynyl, optionally substituted heteroaryl, halogen, NO$_2$, CN, N$_3$, CF$_3$, —ORa, —COORb, —C(O)R$_a$, —N═C═O, —N═CVS, —N(Ra)COORb, —(C$_1$-C$_6$)alkylene-N(Ra)—C(O)—Rb, —(C$_1$-C$_6$)alkylene-N(Ra)—C(O)—(C$_1$-C$_6$)alkylene-Rb, —(C$_1$-C$_6$)alkylene-N(Ra)—C(O)—(C$_1$-C$_6$)alkylene-C(O)O—Rb and maleimidyl,
said (C$_1$-C$_6$)alkyl group being optionally substituted with one or several substituents selected from N$_3$, OH, OCH$_3$, CF$_3$, —O—CH$_2$—O—(C$_1$-C$_6$)alkyl, O—(C$_1$-C$_6$)alkenyl and O—(C$_1$-C$_6$)alkylene-(C$_6$-C$_{10}$)aryl;
Ra is H or (C$_1$-C$_6$)alkyl;
Rb is chosen from the group consisting of: H, (C$_1$-C$_6$) alkyl, and functional groups being able to bind a vector and/or a biomolecule; and Y is a monovalent anion, in particular chosen from: CF$_3$COO, TsO, MsO, NsO, TfO, NO$_3$, Br, Cl, SO$_4$ and BF$_4$.

In one embodiment, in the above mentioned reaction, the diaryliodonium compound is of formula (II) as follows:

(II)

Ar$_1$ and Ar$_2$, independently of each other, are chosen from: (C$_6$-C$_{10}$)aryl and heteroaryl groups, said aryl and heteroaryl groups being substituted with one or several substituents selected from: (C$_1$-C$_6$)alkyl, (C$_2$-C$_6$)alkynyl, optionally substituted heteroaryl, halogen, NO$_2$, CN, N$_3$, CF$_3$, —ORa, —COORb, —C(O)Ra, —N═C═O, —N═C═S, —N(Ra)COORb, —(C$_1$-C$_6$)alkylene-N(Ra)—C(O)—Rb, —(C$_1$-C$_6$)alkylene-N(Ra)—C(O)—(C$_1$-C$_6$)alkylene-Rb, —(C$_1$-C$_6$)alkylene-N(Ra)—C(O)—(C$_1$-C$_6$)alkylene-C(O)O—Rb and maleimidyl,
said (C$_1$-C$_6$)alkyl group being optionally substituted with one or several substituents selected from N$_3$, OH, OCH$_3$, CF$_3$, —O—CH$_2$—O—(C$_1$-C$_6$)alkyl and O—(C$_1$-C$_6$)alkenyl;
Ra being H or (C$_1$-C$_6$)alkyl;
Rb being chosen from the group consisting of: H, (C$_1$-C$_6$)alkyl, succinimidyl, N-hydroxysuccinim idyl, sulfosuccinimidyl, maleimidyl, biotinyl, cyclooctynyl, norbornenyl, cyclopropenyl, bicyclononynyl and trans-cyclooctenyl; and
Y is a monovalent anion, in particular chosen from: CF$_3$COO, TsO, MsO, NsO, TfO, NO$_3$, Br, Cl, SO$_4$ and BF$_4$.

In one embodiment, in the above mentioned reaction, the diaryliodonium compound is of formula (II) as follows:

(II)

Ar$_1$ and Ar$_2$, independently of each other, are chosen from: (C$_6$-C$_{10}$)aryl and heteroaryl groups, said aryl and heteroaryl groups being substituted with one or several substituents selected from: (C$_1$-C$_6$)alkyl, (C$_2$-C$_6$)alkynyl, optionally substituted heteroaryl, halogen, NO$_2$, CN, N$_3$, CF$_3$, —ORa, —COORb, —C(O)Ra, —N═C═O, —N═C═S, —N(Ra)COORb, —(C$_1$-C$_6$)alkylene-N(Ra)—C(O)—Rb, —(C$_1$-C$_6$)alkylene-N(Ra)—C(O)—(C$_1$-C$_6$)alkylene-Rb, —(C$_1$-C$_6$)alkylene-N(Ra)—C(O)—(C$_1$-C$_6$)alkylene-C(O)O—Rb and maleimidyl,
said (C$_1$-C$_6$)alkyl group being optionally substituted with one or several substituents selected from N$_3$, OH, OCH$_3$, CF$_3$, —O—CH$_2$—O—(C$_1$-C$_6$)alkyl and O—(C$_1$-C$_6$)alkenyl and —O—(C$_1$-C$_6$)alkylene-(C$_6$-C$_{10}$)aryl;
Ra being H or (C$_1$-C$_6$)alkyl;
Rb being chosen from the group consisting of: H, (C$_1$-C$_6$)alkyl, succinimidyl, N-hydroxysuccinim idyl, sulfosuccinimidyl, maleimidyl, biotinyl, cyclooctynyl, norbornenyl, cyclopropenyl, bicyclononynyl and trans-cyclooctenyl; and Y is a monovalent anion, in particular chosen from: CF$_3$COO, TsO, MsO, NsO, TfO, NO$_3$, Br, Cl, SO$_4$ and BF$_4$.

In one embodiment, Ra is H or a (C$_1$-C$_4$)alkyl. In another embodiment, Ra is H, methyl, ethyl, propyl or isopropyl. Preferably Ra is H, methyl or isopropyl.

In one embodiment, Rb is being chosen from the group consisting of: H, (C$_1$-C$_6$)alkyl, succinimidyl, N-hydroxysuccinimidyl, sulfosuccinimidyl, maleimidyl and:

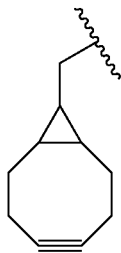 [SMILES: *CC1C2CCC#CCCC12]

In another embodiment, Rb is being chosen from the group consisting of: H, (C$_1$-C$_4$)alkyl, succinimidyl, N-hydroxysuccinimidyl and maleimidyl, more particularly Rb is succinimidyl or maleimidyl.

In one embodiment, when Ar$_1$ and/or Ar$_2$ is substituted by a heteroaryl, said heteroaryl is optionally substituted one or more times by a (C$_1$-C$_6$)alkyl, preferably a methyl.

In one embodiment, Ar$_1$ and Ar$_2$ are not identical (i.e. not symmetrical). In one embodiment, Ar$_1$ and Ar$_2$, independently of each other, are chosen from the group consisting of phenyl and (5-6)-membered heteroaryl containing from 1 to 4 heteroatom(s) selected from O, S or N, said phenyl and (5-6)-membered heteroaryl being substituted with one or several substituents selected from: (C$_1$-C$_6$)alkyl, (C$_2$-C$_6$)alkynyl, 5-membered heteroaryl containing from 1 to 4 heteroatom(s) selected from O, S or N, halogen, NO$_2$, CN, N$_3$, CF$_3$, ORa, COORb, C(O)Ra, —N=C=O, —N=C=S, —N(Ra)COORb, —(C$_1$-C$_6$)alkylene-N(Ra)—C(O)—Rb, —(C$_1$-C$_6$)alkylene-N(Ra)—C(O)—(C$_1$-C$_6$)alkylene-Rb, (C$_1$-C$_6$)alkylene-N(Ra)—C(O)—(C$_1$-C$_6$)alkylene-C(O)O—Rb and maleimidyl,
said (C$_1$-C$_6$)alkyl group being optionally substituted with one or several substituents selected from N$_3$, OH, OCH$_3$, CF$_3$, O—CH$_2$—O—(C$_1$-C$_6$)alkyl and —O—(C$_1$-C$_6$)alkenyl; and Ra and Rb being defined as above.

In one embodiment, Ar$_1$ and Ar$_2$, independently of each other, are chosen from the group consisting of phenyl and (5-6)-membered heteroaryl containing from 1 to 4 heteroatom(s) selected from O, S or N, said phenyl and (5-6)-membered heteroaryl being substituted with one or several substituents selected from: (C$_1$-C$_6$)alkyl, (C$_2$-C$_6$)alkynyl, 6-membered heteroaryl containing from 1 to 4 heteroatom(s) selected from O, S or N, halogen, NO$_2$, CN, N$_3$, CF$_3$, ORa, COORb, C(O)Ra, —N=C=O, —N=C=S, —N(Ra)CO-ORb, —(C$_1$-C$_6$)alkylene-N(Ra)—C(O)—Rb, —(C$_1$-C$_6$)alkylene-N(Ra)—C(O)—(C$_1$-C$_6$)alkylene-Rb, (C$_1$-C$_6$)alkylene-N(Ra)—C(O)—(C$_1$-C$_6$)alkylene-C(O)O—Rb and maleimidyl,
said (C$_1$-C$_6$)alkyl group being optionally substituted with one or several substituents selected from N$_3$, OH, OCH$_3$, CF$_3$, O—CH$_2$—O—(C$_1$-C$_6$)alkyl, —O—(C$_1$-C$_6$)alkenyl and —O—(C$_1$-C$_6$)alkylene-(C$_6$-C$_{10}$)aryl; and Ra and Rb being defined as above.

In another embodiment, Ar$_1$ and Ar$_2$ are independently of each other a phenyl or a thiophene, said phenyl and thiophene being substituted with one or several substituents selected from: methyl, (C$_2$)alkynyl, Br, Cl, I, At, NO$_2$, CN, N$_3$, OCH$_3$, —O-isopropyl, —C(O)O-succinimidyl, —C(O)O—CH$_2$—CH$_3$, and maleimidyl,
said methyl group being optionally substituted with one or several substituents selected from N$_3$, OH, OCH$_3$, CF$_3$ and —O—CH$_2$—CH=CH$_2$.

In another embodiment, Ar$_1$ and Ar$_2$ are independently of each other a phenyl or a thiophene, said phenyl and thiophene being substituted with one or several substituents selected from: methyl, (C$_2$)alkynyl, Br, Cl, I, At, NO$_2$, CN, N$_3$, OCH$_3$, —O-isopropyl,
—C(O)O-succinimidyl, —C(O)O—OH$_2$—OH$_3$, maleimidyl, optionally substituted tetrazine,

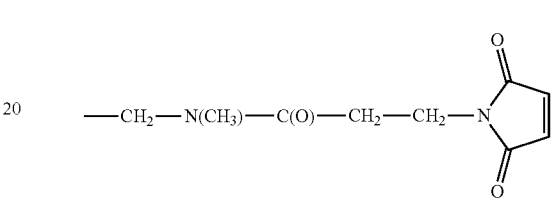

and said methyl group being optionally substituted with one or several substituents selected from N$_3$, OH, OCH$_3$, CF$_3$, —O—OH$_2$—CH=CH$_2$ and

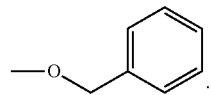

In one embodiment, the aryl and heteroaryl groups of Ar$_1$ and Ar$_2$ are substituted one or two times, preferably by the substituents independently chosen from the group consisting of: (C$_1$-C$_6$)alkyl, (C$_2$-C$_6$)alkynyl, 6-membered heteroaryl containing from 1 to 4 heteroatom(s) selected from O, S or N and substituted by a (C$_1$-C$_6$)alkyl; halogen, NO$_2$, ON, N$_3$, CF$_3$, ORa, COORb, C(O)Ra, and maleimidyl,
said (C$_1$-C$_6$)alkyl group being optionally substituted with one or several substituents selected from N$_3$, OH, OCH$_3$, OF$_3$, and O—CH$_2$—CH=CH$_2$; and Ra and and Rb being defined as above.

In one embodiment, Ar$_1$ and Ar$_2$ are independently from each other phenyl or thiophene groups, substituted by ORa, (C$_1$-C$_6$)alkyl, (C$_2$-C$_6$)alkynyl, N$_3$ and C(O)O-succinimidyl; said (C$_1$-C$_6$)alkyl group being optionally substituted by N$_3$ and Ra being defined as above.

In one embodiment, Ar$_1$ or Ar$_2$ is a phenyl substituted from one to five times, preferably three times, by CH$_3$ and/or OCH$_3$.

In one embodiment, the diaryliodonium compound is of formula (II-1):

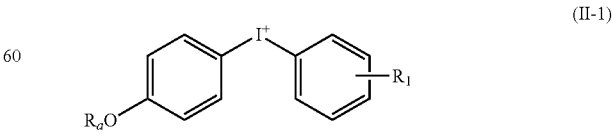

wherein:
R$_1$ is chosen from the group consisting of: (C$_1$-C$_6$)alkyl, (C$_2$-C$_6$)alkynyl, optionally substituted heteroaryl, halogen, NO₂, CN, N₃, CF₃, —ORa, —COORb, —C(O)Ra, —N=C=O, —N=C=S, —N(Ra)COORb, —(C₁-C₆)alkylene-N(Ra)—C(O)—Rb, —(C₁-C₆)alkylene-N(Ra)—C(O)—(C₁-C₆)alkylene-Rb, —(C₁-C₆)alkylene-N(Ra)—C(O)—(C₁-C₆)alkylene-C(O)O—Rb and maleimidyl, said (C₁-C₆)alkyl group being optionally substituted with one or several substituents selected from N₃, OH, OCH₃, CF₃, and O—CH₂—CH=CH₂;

Ra and Rb being defined as above.

In one embodiment, R₁ is chosen from the group consisting of: methyl, (C₂)alkynyl, halogen, NO₂, CN, N₃, OCH₃, O-isopropyl, C(O)O-succinimidyl, C(O)O—CH₂—CH₃, C(O)—N-hydroxysuccinimidyl, and maleimidyl, said methyl group being optionally substituted with one or several substituents selected from N₃, OH, OCH₃, CF₃, and O—CH₂—CH=CH₂.

In one embodiment, R₁ is chosen from the group consisting of: ORa, (C₁-C₆)alkyl, (C₂-C₆)alkynyl, N₃ and C(O)O-succinimidyl; said (C₁-C₆)alkyl group being optionally substituted by N₃ and Ra being defined as above.

In one embodiment, the diaryliodonium compound is of formula (II-2):

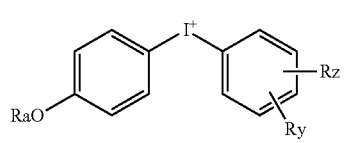
(II-2)

wherein:

Ry and Rz are independentlyl of each other chosen from the group consisting of: (C₁-C₆)alkyl, (C₂-C₆)alkynyl, —(C₁-C₆)alkylene-N(Ra)—C(O)—Rb, —(C₁-C₆)alkylene-N(Ra)—C(O)—(C₁-C₆)alkylene-Rb, said (C₁-C₆)alkyl group being optionally substituted with one or several substituents selected from N₃, OH, OCH₃, CF₃, O—CH₂—CH=CH₂ and

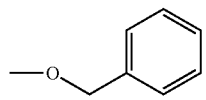

Ra being defined as above.

In one embodiment, r is TsO⁻ or TfO⁻. In another embodiment, Y⁻ is TsO⁻, TfO⁻ or BF4⁻.

In one embodiment, in the reaction as defined above, the diaryliodonium compound of formula (II) is selected from the following compounds:

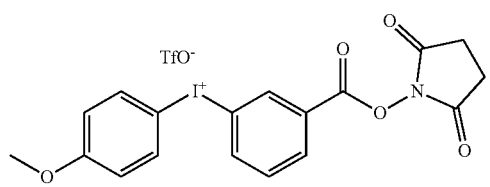

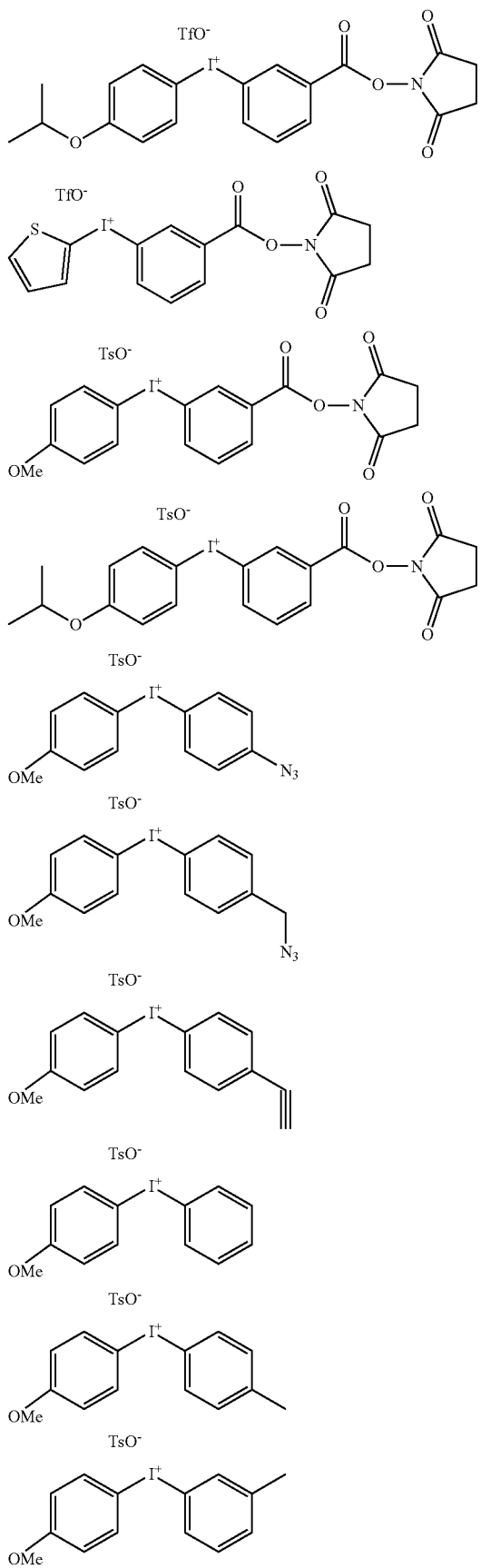

-continued

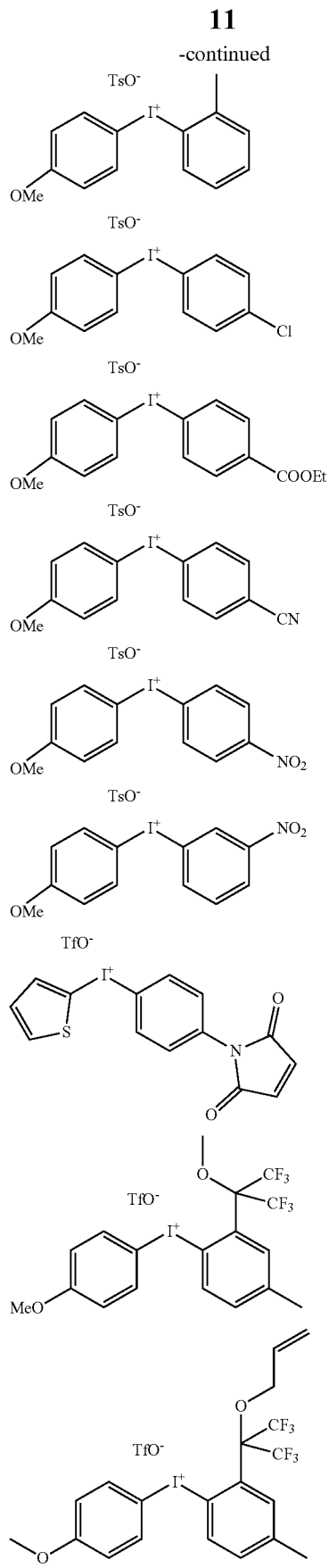

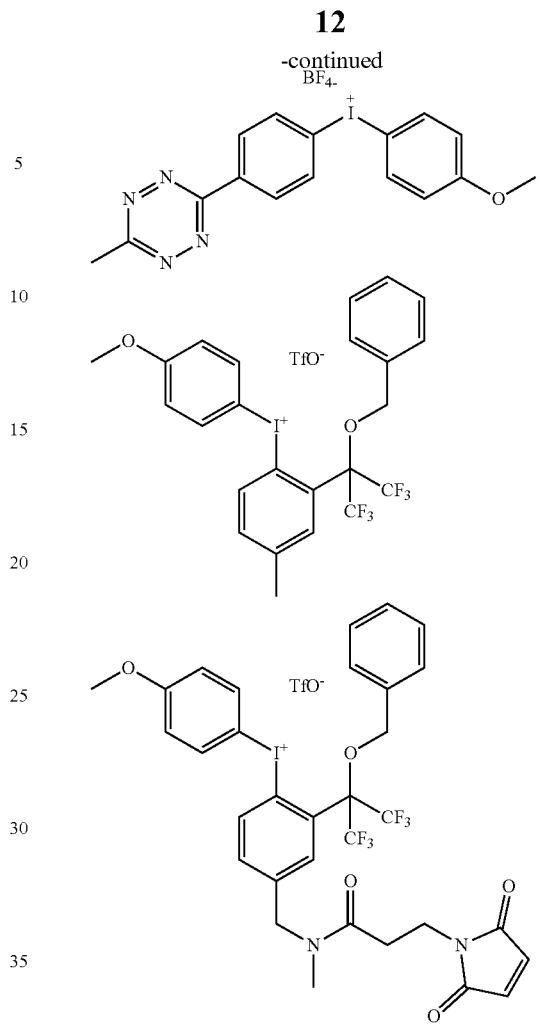

In one embodiment of the reaction defined above, the iodo- or astatoarene is of formula (I):

$$Ar-X \quad (I)$$

wherein:
X is I or At; and
Ar is $Ar_1$ or $Ar_2$ as defined above.

In one embodiment, X is radioactive. In one embodiment, X is chosen from the group consisting of $^{123}I$, $^{124}I$, $^{125}I$, $^{131}I$ and $^{211}At$. Preferably X is $^{211}At$ or $^{125}I$. In a particular embodiment, X is At, preferably $^{211}At$.

In another embodiment of the reaction defined above, the iodo- or astatoarene is of formula (I-1):

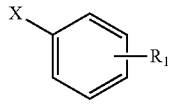

(I-1)

wherein:
X is I or At; and
$R_1$ is as defined above.

In one embodiment, in the diaryliodonium compounds of formulae (II), (II-1) and (II-2) and in the iodo- or astatoarene of formulae (I) and (I-1), the halogen is represented by the Cl, Br, I and At atoms. In one embodiment, the diaryliodonium compounds of formulae (II), (II-1) and (II-2) and the iodo- or astatoarene of formulae (I) and (I-1) do not comprise a fluorine atom. In one embodiment, the diaryliodonium compounds of formulae (II) and (II-1) and the iodo- or astatoarene of formulae (I) and (I-1) do not comprise more than one fluorine atom.

In another embodiment of the reaction defined above, the iodide or astatide salt is of formula (III):

$$A^+X^- \quad \text{(III)}$$

wherein:
X is as defined above; and
A is a monovalent cation selected among Na, K, Cs, tetraalkylammonium and tetraalkylphosphonium.

In one embodiment of the reaction defined above, the reaction is carried out in a solvent selected from the group consisting of: acetonitrile, an alcohol such as methanol, dimethylformamide, water, and mixtures thereof, preferably a mixture of acetonitrile and water or acetonitrile. In one embodiment of the astatination reaction defined above, the reaction is carried out in a solvent selected from the group consisting of: methanol, water, and mixtures thereof.

In one embodiment of the reaction defined above, the reaction is carried out in the presence of water. In one embodiment, the reaction is carried out in the presence of a base such as NaOH, KOH, LiOH, CsOH, $K_2CO_3$, $Na_2CO_3$, $Cs_2CO_3$ or mixtures thereof. Preferably, a base would be used when the diaryliodonium salt according to the invention does not comprise a hydrolysable functional group such as an ester group.

In a particular embodiment, in the case of iodination, acetonitrile or a mixture of acetonitrile and water is used as solvent, preferably at a temperature comprised between 60° C. and 140° C., preferably between 90° C. and 130° C., for example about 120° C. In another particular embodiment, in the case of astatination, water, methanol, acetonitrile or mixture thereof is used as solvent, preferably at a temperature below 150° C., for example comprised between 20 and 125° C. In one embodiment, in the case of astatination, the temperature is comprised between 40° C. and 100° C.

In one embodiment of the reaction defined above, the water comprised in the solvent is not evaporated. In one embodiment, the reaction is performed in the presence of a catalyst, for example a Cu+ or a $Cu^{2+}$ salt.

In particular, the astatination reaction can be performed in the presence of water and at low temperature (from 40° C. to 100° C. for example), contrary to the $^{18}F$ reaction. High yields (for example above 60%) are obtained with these conditions for the astatination reaction.

Purification Step

In one embodiment, the method according to the invention further comprises a purification step wherein a iodo- or astatoarene, preferably of formula (I) or (I-1), is extracted by a solvent in which:
an astatide or iodide salt, preferably of formula (III), and the diaryliodonium salt of formula (II) or (II-1) are insoluble, and
said iodo- or astatoarene, preferably of formula (I) or (I-1), is soluble.

In one embodiment, the solvent is chosen from diethylether; alkane such as hexane, cyclohexane or heptane; a mixture of diethylether and alkane; a mixture of alkane and ethyl acetate; or a mixture of alkane and ethyl acetate, preferably diethylether.

In another embodiment, the solvent is chosen from diethylether; alkane such as hexane, cyclohexane or heptane; toluene; a mixture of diethylether and alkane; a mixture of alkane and ethyl acetate; or a mixture of alkane and ethyl acetate, preferably diethylether In one embodiment, said purification step is repeated from one to five times.

In one embodiment, said purification step comprises the following steps:
  i) evaporation to dryness of a solution comprising a iodo- or astatoarene, preferably of formula (I) or (I-1) and optionally comprising the corresponding diaryliodonium salt of formula (II) or (II-1) and an astatine or iodine salt, preferably of formula (III);
  ii) addition of diethylether; and
  iii) evaporation to dryness, said iodo- or astatoarene being extracted by diethylether.

In one embodiment, in step iii), the extraction can be performed with toluene.

In one embodiment, the method as defined above does not comprise a purification step involving a chromatography such as a High Performance Liquid Chromatogaphy (HPLC) or a silica gel chromatography.

Reduction Step of the Astatine

In one embodiment, the method defined above previously comprises a step of reduction of astatine. In one embodiment, the reduction is performed in a solution. The solvent may be acetonitrile; chloroform; an alcohol such as methanol; dimethylformamide; water; and mixtures thereof; preferably water; a mixture of acetonitrile and water; or chloroform.

In a particular embodiment, the reduction step comprises the following steps:
  i) preparing a solution of astatine with a solvent as defined above (i.e. in the reduction step), preferably with acetonitrile;
  ii) mixing the solution obtained in step i) with a solution comprising a reducing agent, preferably an aqueous solution, thereby obtaining a solution of an astatide salt.

In another embodiment, the reduction step comprises the following steps:
  i) preparing a solution of astatine with a solvent as defined above, preferably with chloroform;
  ii) evaporating to dryness the solution obtained in step i), preferably under a stream of $N_2$; and
  iii) mixing the obtained dry residue of astatine with a solution comprising a reducing agent, preferably with an aqueous solution.

In one embodiment, the astatide salt is the astatide salt of formula (III) as defined above.

In one embodiment, the reduction is performed with a reducing agent chosen from the group consisting of: $Na_2SO_3$, $Na_2S_2O_5$, $Na_2S_2O_3$, ascorbate, cysteine and hydrazine, preferably $Na_2SO_3$.

In a particular embodiment, the method according to the invention comprises the following steps:
  a) in case of astatination, a step of reduction of astatine as defined above, thereby obtaining an astatide salt;
  b) the reaction of a diaryliodonium salt of formula (II) or (II-1) as defined above with said astatide salt or a iodide salt, thereby obtaining the iodo- or astatoarene of formula (I) or (I-1) respectively; and
  c) a purification step as defined above wherein the iodo- or astatoarene of formula (I) or (I-1) is extracted by a solvent (defined above for the purification step).

In another particular embodiment, the method according to the invention comprises the following steps:
  a) in case of astatination, a step of reduction of astatine as defined above, thereby obtaining an astatide salt of formula (III) as defined above;

b) the reaction of a diaryliodonium salt of formula (II) or (II-1) as defined above with said astatide salt or a iodide salt of formula (III), thereby obtaining the iodo- or astatoarene of formula (I) or (I-1) respectively; and c) a purification step as defined above wherein the iodo- or astatoarene of formula (I) or (I-1) is extracted by diethylether.

In one embodiment, in step c), the extraction can be performed with toluene.

By "astatination" is meant the synthesis of an astatoarene according to the invention, in particular when X is At, in particular $^{211}$At, in the compounds of formulae (I), (I-1) and (III).

Diaryliodonium of formulae (II), (II-1) and (II-2)

In another aspect, the invention relates to diaryliodonium salts of formulae (II) and (II-1) defined as above, as such. In particular, the diaryliodonium salt of formula (II) is selected from one of the following specific compounds:

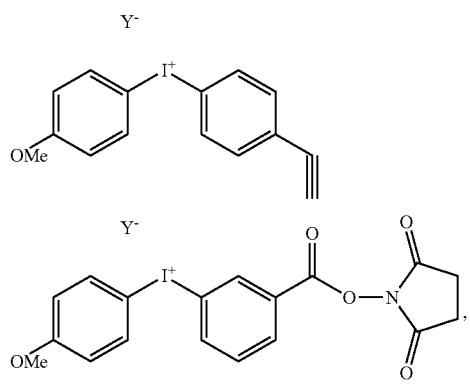

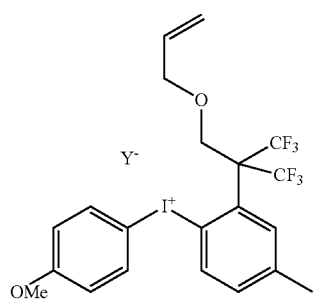

the monovalent anion Y$^-$ being as defined above, preferably TsO$^-$ or TfO$^-$.

In particular, the diaryliodonium salt of formula (II) is selected from one of the following specific compounds:

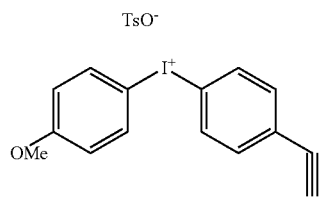

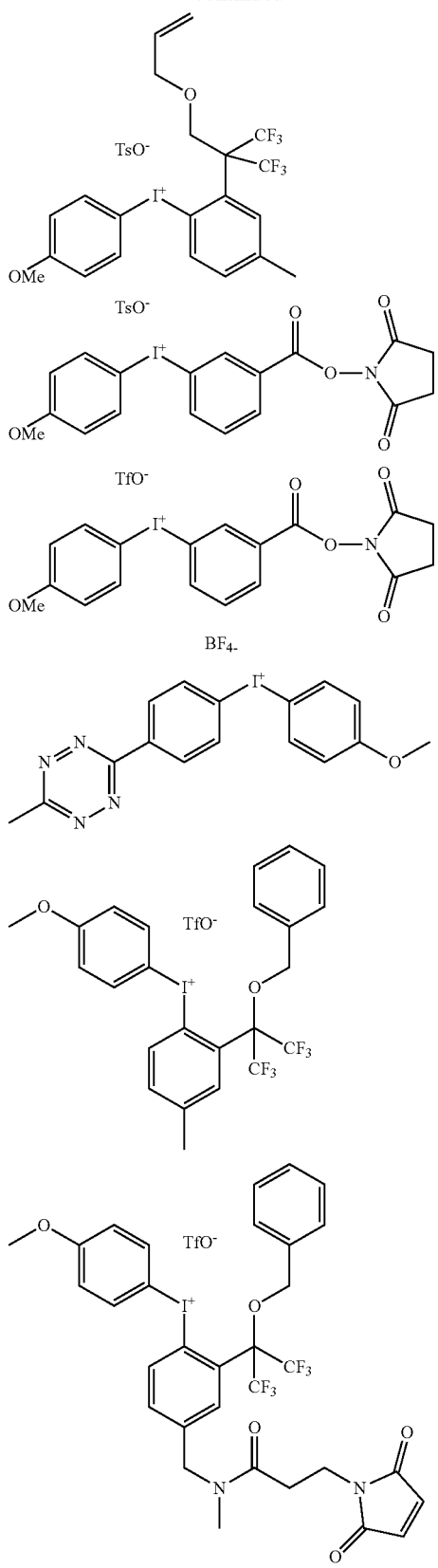

In particular, the diaryliodonium salt of formula (II) is selected from one of the following compounds:

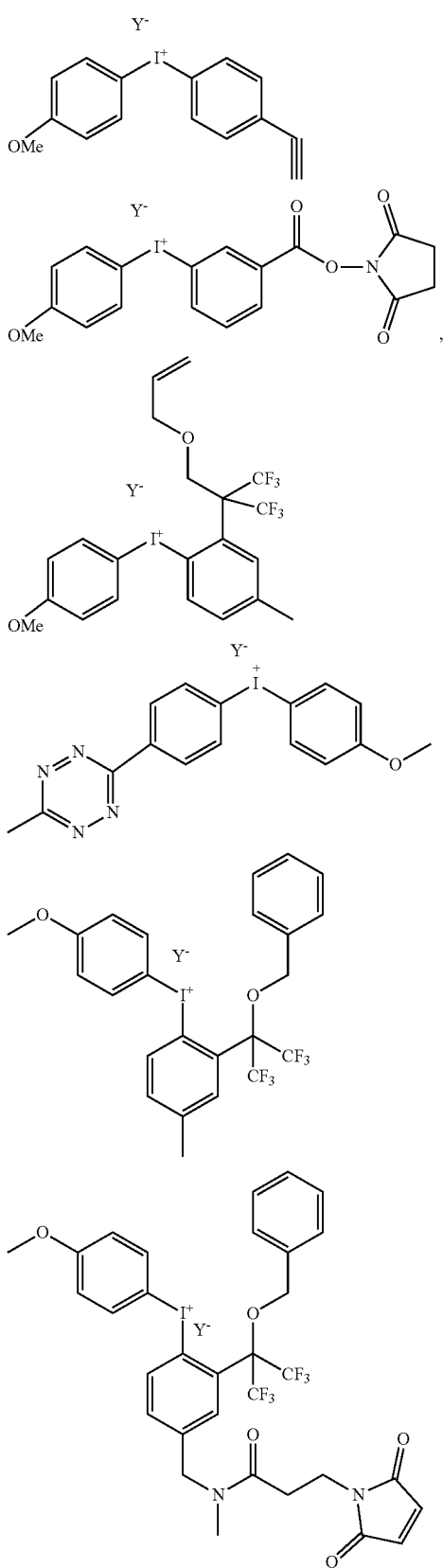

the monovalent anion Y⁻ being as defined above, preferably BF4⁻, TsO⁻ or TfO⁻.

Iodo- and Astatoarene of Formula (I), (I-1) and (I-3)

The invention also relates to iodo- and astatoarene compounds, having the following formula (I-2):

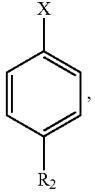

(I-2)

X being as defined above and $R_2$ being chosen from the group consisting of ethynyl, $N_3$ and —$CH_2$—$N_3$.

The invention also relates to iodo- and astatoarene compounds, having the following formula (I-3):

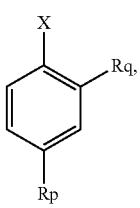

(I-3)

X being as defined above, $R_p$ being an optionally substituted tetrazine, a $(C_1-C_6)$alkyl or a —$(C_1-C_6)$alkylene-N(Ra)—C(O)—$(C_1-C_6)$alkylene-Rb and Rq being H or a $(C_1-C_6)$alkyl optionally substituted with one or several substituents selected from $N_3$, OH, $OCH_3$, $CF_3$, —O—$CH_2$—O—$(C_1-C_6)$alkyl, —O—$(C_1-C_6)$alkenyl and —O—$(C_1-C_6)$alkylene-$(C_6-C_{10})$aryl;

The invention also relates to iodo- and astatoarene compounds of formula (I), having one of the following formulae:

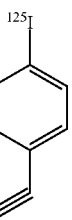

a

b

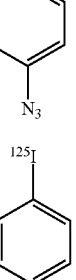

c

-continued d 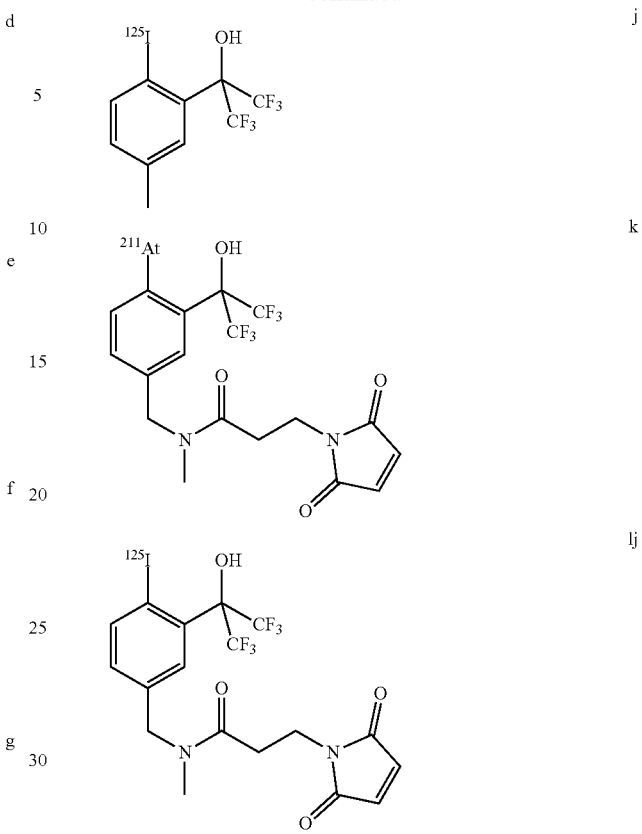

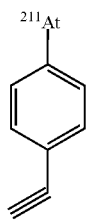
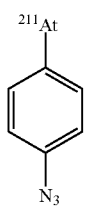
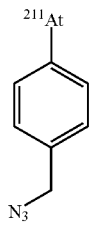
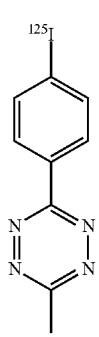
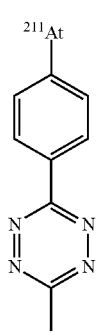
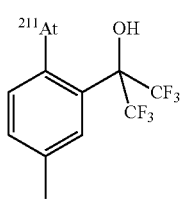

Radiolabelling Method

The present invention also relates to a method of synthesizing a iodo- or astatolabelled biomolecule and/or vector comprising the steps of:
 (i) synthesizing a iodo- or astatoarene according to the method defined above; and
 (ii) reacting said iodo- or astatoarene with a biomolecule and/or a vector carrying a functional group reactive with said iodo- or astatoarene.

In one embodiment, the iodo- or astatoarene is of formula (I) or (I-1) as previously defined.

"By functional group reactive with said iodo or astatoarene", it is meant amino, thiol and bioorthogonal functions such as $N_3$, alkyne and strained alkene. A chemical reaction is is called "bioorthogonal" if it can take place in a complex biological medium without altering it.

In one embodiment, in the radiolabelling method defined above, X is radioactive in the compounds of formulae (I) and (I-1). In one embodiment, X is chosen from the group consisting of $^{123}I$, $^{124}I$, $^{125}I$, $^{131}I$ and $^{211}At$. In a particular embodiment, X is $^{211}At$. In another particular embodiment, X is $^{125}I$.

The methods of coupling are well known by a man skilled in the art and may be found in the following references:

David M. Wong and Shan S. Jameson, Chemistry of Protein and Nucleic Acid Cross-Linking and Conjugation Second Edition, CRC Press 2011 (N.Y.), 604 p.;

N. L. Benoiton, Peptide Bond Formation: Active Esters in HoubenWeyl Methods of Organic Chemistry Synthesis of Peptides and Peptidomimetics (2001), WORKBENCH EDITION;

Emmanuel Basle, Nicolas Joubert and Mathieu Pucheault, Protein Chemical Modification on Endogenous Amino Acids, Chemistry & Biology (2010), Volume 17, Issue 3, 213-227;

Sletten, E. M.; Bertozzi, C. R. Bioorthogonal Chemistry: Fishing for Selectivity in a Sea of Functionality. Angew. Chem. Int. Ed. (2009), 48, 6974-6998;

Shuang Liu, Bifunctional Coupling Agents for Radiolabeling of Biomolecules and Target-Specific Delivery of Metallic Radionuclides, Advanced Drug Delivery Reviews, Volume 60, Issue 12, 15 Sep. 2008, Pages 1347-1370;

Wu A M, Senter P D, Arming antibodies: prospects and challenges for immunoconjugates. Nat Biotechnol 2005, 23:1137-1146; and Alan R. Fritzberg, Ronald W. Berninger, Stephen W. Hadley and Dennis W. Wester, Approaches to Radiolabeling of Antibodies for Diagnosis and Therapy of Cancer, Pharmaceutical Research (1988), Volume 5, Number 6, 325-334.

These methods are also known as conjugation methods wherein the compound of formula (I) or (I-1), linked to a vector and/or a biomolecule, is called "a conjugate".

The present invention relates to a conjugate comprising at least one iodo- or astatoarene according to the invention, covalently linked to a vector or a biomolecule through the functional group of said iodo- or astatoarene.

Lastly, the invention concerns a radiolabelling kit comprising:
a diaryliodonium compound of formula (II) or (II-1) as defined above,
optionally a reducing agent as defined above,
optionally an iodide or astatide salt, preferably of formula (III) as defined above, and
optionally a biomolecule and/or a vector as previously defined.

The invention also relates to a method of synthesizing a iodo- or astatoarene comprising the reaction of a diaryliodonium compound with a iodide or astatide salt, respectively, wherein the diaryliodonium compound is of formula (II):

(II)

wherein:
Ar$_1$ and Ar$_2$, independently of each other, are chosen from: (C$_6$-C$_{10}$)aryl and heteroaryl groups, said aryl and heteroaryl groups being substituted with one or several substituents selected from: (C$_1$-C$_6$)alkyl, (C$_2$-C$_6$)alkynyl, optionally substituted heteroaryl, halogen, NO$_2$, CN, N$_3$, CF$_3$, —ORa, —COORb, —C(O)R$_a$, —N=C=O, —N=C=S, —N(Ra)COORb, —(C$_1$-C$_6$)alkyl-N(Ra)—C(O)—Rb, —(C$_1$-C$_6$)alkyl-N(Ra)—C(O)—(C$_1$-C$_6$)alkyl-Rb, —(C$_1$-C$_6$)alkyl-N(Ra)—C(O)—(C$_1$-C$_6$)alkyl-C(O)O—Rb and maleimide,
said (C$_1$-C$_6$)alkyl group being optionally substituted with one or several substituents selected from N$_3$, OH, OCH$_3$, CF$_3$, —O—CH$_2$—O—(C$_1$-C$_6$)alkyl and —O—(C$_1$-C$_6$)alkene;
Ra is H or (C$_1$-C$_6$)alkyl;
Rb is chosen from the group consisting of: H, (C$_1$-C$_6$) alkyl, and functional groups being able to bind a vector and/or a biomolecule; and
Y is a monovalent anion, in particular chosen from: CF$_3$COO, TsO, MsO, NsO, TfO, NO$_3$, Br, Cl, SO$_4$ and BF$_4$.

Figure 1:
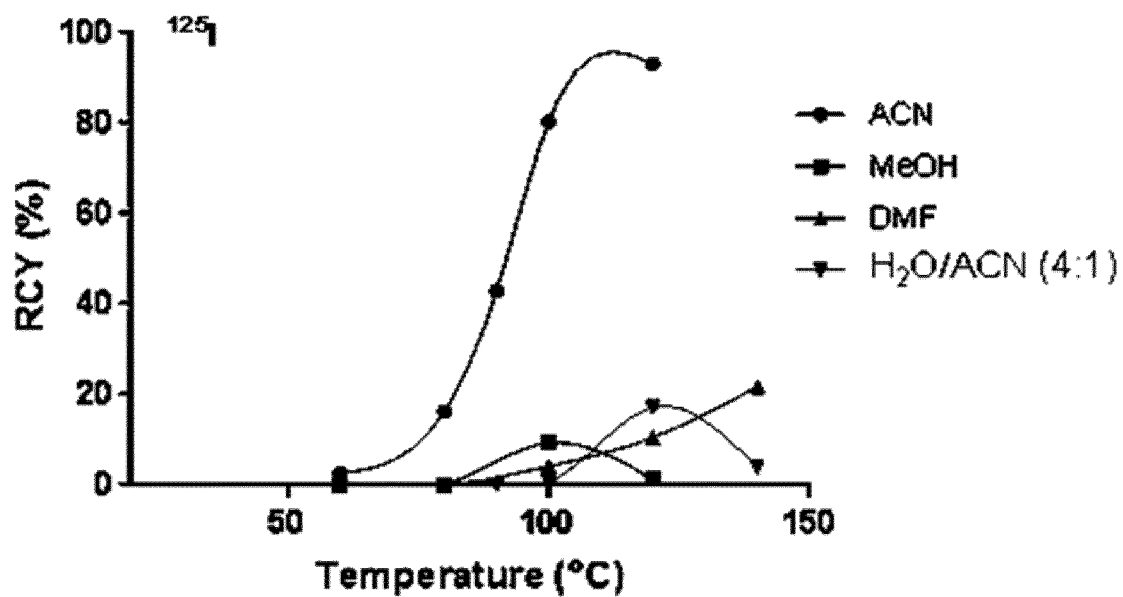
FIG. 1 shows the percentage of the radiochemical yield (RCY) of the iodination reaction depending on the solvent and temperature used.

Some examples are given below, without limitation of the present invention.

EXAMPLES

RCY means radiochemical yield.
ACN means acetonitrile.

Example 1

Synthesis of Diaryliodonium Salts of Formula (II)

All reagents and solvents were obtained commercially and used without further purification unless otherwise noted. $^1$H NMR and $^{13}$C NMR spectra were recorded on a Bruker Advance 300 MHz instrument, and chemical shifts are reported in ppm on the δ scale relative to TMS. Electrospray ionization-mass spectra (ESI-MS) were acquired using an Agilent LC/MSD system equiped with a multimode ion. Elemental analyses were performed by Galbraith Lab. Inc. (Knoxville, Tenn.) using combustion analysis methods for C, H, and N.

1. General Method for the Preparation of the aryl-4-methoxyphenyliodonium tosylates, Compounds of Formula (II)

3-chloroperbenzoic acid dried in vacuo for 1 h prior to use (1.77 mmol) was dissolved in CHCl$_3$ (15 mL) and the iodoaryl was added (1.5 mmol). The solution was stirred at rt for 15 min. and turned slightly yellow and cloudy. 4-toluenesulfonic acid hydrate (1.77 mmol) and anisole (8.05 mmol) were then added and the solution was heated for 2 h30 at 40° C., turning bright yellow. The solvent was evaporated in vacuo and the oily residue was triturated in Et$_2$O until it turned into a solid. The solid was redissolved in the minimum amount of MeOH and Et$_2$O was added until the solution became cloudy. It was placed in the fridge at 4° C. until the iodonium tosylate precipitates or crystallizes.

1.1. Phenyl(4-methoxyphenyl)iodonium tosylate

White solid (47%). $^1$H NMR (CDCl$_3$, 300 MHz, ppm): δ 2.02 (s, 1H, broad), 2.30 (s, 3H), 3.78 (s, 3H), 6.83 (d, 2H, J=9.0 Hz), 7.02 (d, 2H, J=7.8 Hz), 7.29-7.34 (m, 2H), 7.44-7.52 (m, 3H), 7.85-7.92 (m, 4H). $^{13}$C NMR (CDCl$_3$, 75 MHz, ppm): δ 21.5, 55.8, 104.1, 116.0, 117.7, 126.2, 128.7, 131.6, 131.8, 134.7, 137.6, 139.5. ESI-MS: m/z=311.0 [M-OTs]$^+$, 793.0 [2M-OTs]$^+$. Mp: 154° C. C$_{20}$H$_{19}$IO$_4$S, calculated: C, 49.80; H, 3.97. Found: C, 49.97; H, 3.88.

1.2. 4-tolyl(4-methoxyphenyl)iodonium tosylate

Colorless crystals (77%). $^1$H NMR (CDCl$_3$, 300 MHz, ppm): δ 2.04 (s, 1H, broad), 2.31 (s, 3H), 2.33 (s, 3H), 3.78 (s, 3H), 6.81 (d, 2H, J=9.3 Hz), 7.02 (d, 2H, J=8.1 Hz), 7.11 (d, 2H, J=8.4 Hz), 7.52 (d, 2H, J=8.1 Hz), 7.79 (d, 2H, J=8.4 Hz), 7.85 (d, 2H, J=9.3 Hz). $^{13}$C NMR (CDCl$_3$, 75 MHz, ppm): δ 21.4, 21.5, 55.8, 104.1, 112.2, 117.6, 126.2, 128.6, 132.6, 134.7, 137.3, 139.4, 142.5, 143.0, 162.4. ESI-MS: m/z=325.0 [M-OTs]+, 821.0 [2M-OTs]+. Mp: 169° C. $C_{21}H_{21}IO_4S$, calculated: C, 50.82; H, 4.26. Found: C, 51.07; H, 4.03.

1.3. 3-tolyl(4-methoxyphenyl)iodonium tosylate

Colorless crystals (69%). $^1$H NMR (CDCl$_3$, 300 MHz, ppm): δ 1.93 (S, 1H, broad), 2.29 (s, 3H), 2.31 (s, 3H), 3.79 (s, 3H), 6.84 (d, 2H, J=9.3 Hz), 7.04 (d, 2H, J=8.1 Hz), 7.18-7.29 (m, 2H), 7.54 (d, 2H, J=8.1 Hz), 7.68 (d, 1H, J=8.1 Hz), 7.74 (S, 1H), 7.87 (d, 2H, J=9.3 Hz). $^{13}$C NMR (CDCl$_3$, 75 MHz, ppm): δ 21.4, 21.5, 55.8, 103.8, 115.7, 117.7, 126.2, 128.6, 131.5, 131.7, 132.6, 135.1, 137.5, 139.4, 142.4, 143.1, 162.5. ESI-MS: m/z=325.0 [M-OTs]+, 821.0 [2M-OTs]+. Mp: 123° C. $C_{21}H_{21}IO_4S$, calculated: C, 50.82; H, 4.26. Found: C, 50.89; H, 4.24.

1.4. 2-tolyl(4-methoxyphenyl)iodonium tosylate

Colorless crystals (82%). $^1$H NMR (CDCl$_3$, 300 MHz, ppm): δ 2.17 (S, 1H, broad), 2.29 (s, 3H), 2.55 (s, 3H), 3.76 (s, 3H), 6.79 (d, 2H, J=9.3 Hz), 6.99 (d, 2H, J=8.1 Hz), 7.10-7.15 (m, 1H), 7.32 (d, 1H, J=6.6 Hz), 7.39-7.46 (m, 3H), 7.79 (d, 2H, J=9 Hz), 8.1 (m, 1H). $^{13}$C NMR (CDCl$_3$, 75 MHz, ppm): δ 21.5, 25.8, 55.7, 103.5, 117.5, 120.9, 126.1, 128.6, 129.2, 131.6, 132.7, 136.7, 137.5, 129.3, 141.3, 143.0, 162.2. ESI-MS: m/z=325.0 [M-OTs]+, 821.0 [2M-OTs]+. Mp: 155° C. $C_{21}H_{21}IO_4S$, calculated: C, 50.82; H, 4.26. Found: C, 50.90; H, 4.19.

1.5. 4-chlorophenyl(4-methoxyphenyl)iodonium tosylate

White solid (80%). $^1$H NMR (DMSO-d$_6$, 300 MHz, ppm): δ 2.29 (s, 3H), 3.80 (s, 3H), 7.06-7.12 (m, 4H), 7.47 (d, 2H, J=7.8 Hz), 7.59 (d, 2H, J=8.4 Hz), 8.16-8.22 (m, 4H). $^{13}$C NMR (DMSO-d$_6$, 75 MHz, ppm): δ 20.8, 55.7, 105.7, 114.9, 117.5, 125.5, 128.0, 131.6, 136.6, 137.1, 137.2, 137.6, 145.7, 162.0. ESI-MS: m/z=344.9/346.9 [M-OTs]+, 860.9/862.9 [2M-OTs]+. Mp: 186° C. $C_{20}H_{18}ClIO_4S$, calculated: C, 46.48; H, 3.51. Found: C, 46.54; H, 3.39.

1.6. 4-(ethoxycarbonyl)phenyl(4-methoxyphenyl)iodonium tosylate

White solid (59%). $^1$H NMR (CDCl$_3$, 300 MHz, ppm): δ 1.36 (t, 3H, J=7.0 Hz), 2.25 (s, 1H, broad), 2.29 (s, 3H), 3.77 (s, 3H), 4.35 (q, 2H, J=7.0 Hz), 6.79 (d, 2H, J=9.0 Hz), 6.97 (d, 2H, J=7.8 Hz), 7.49 (d, 2H, J=8.1 Hz), 7.84-7.92 (m, 4H), 7.99 (d, 2H, J=8.1 Hz). $^{13}$C NMR (CDCl$_3$, 75 MHz, ppm): δ 14.4, 21.4, 55.7, 61.8, 104.5, 117.6, 121.0, 126.1, 128.6, 132.1, 133.1, 134.8, 137.9, 139.5, 142.6, 162.5, 165.3. ESI-MS: m/z=383.0 [M-OTs]+, 937.0 [2M-OTs]+. Mp: 137° C. $C_{23}H_{23}IO_6S$, calculated: 0, 49.83; H, 4.18. Found: C, 49.78; H, 4.14.

1.7. 4-nitrophenyl(4-methoxyphenyl)iodonium tosylate

White solid (36%). $^1$H NMR (DMSO-d$_6$, 300 MHz, ppm): δ 2.29 (s, 3H), 3.80 (s, 3H), 7.08-7.11 (m, 4H), 7.47 (d, 2H, J=8.1 Hz), 8.22-8.30 (m, 4H), 8.42 (d, 2H, J=8.7 Hz). $^{13}$C NMR (DMSO-d$_6$, 75 MHz, ppm): δ 20.8, 55.8, 117.6, 117.6, 123.2, 125.5, 126.1, 128.0, 136.0, 137.6, 145.8, 149.2, 162.2. ESI-MS: m/z=355.9 [M-OTs]+, 883.0 [2M-OTs]+. Mp: 192° C. $C_{20}H_{18}INO_6S+\frac{1}{2}H_2O$, calculated: C, 44.79; H, 3.57; N, 2.61. Found: C, 44.70; H, 3.18; N, 2.38.

1.8. 3-nitrophenyl(4-methoxyphenyl)iodonium tosylate

White solid (35%). $^1$H NMR (DMSO-d$_6$, 300 MHz, ppm): δ 2.28 (s, 3H), 3.80 (s, 3H), 7.10 (m, 4H), 7.46 (d, 2H, J=7.8 Hz), 7.79 (m, 1H), 8.26 (d, 2H, J=8.7 Hz), 8.43 (d, 1H, J=7.8 Hz), 8.59 (d, 1H, J=7.8 Hz), 9.12 (s, 1H). $^{13}$C NMR (DMSO-d$_6$, 75 MHz, ppm): δ 20.8, 55.7, 105.9, 116.9, 117.6, 125.5, 126.5, 128.0, 129.5, 132.6, 137.5, 137.6, 140.8, 145.7, 148.2, 162.2. ESI-MS: m/z=355.9 [M-OTs]+, 883.0 [2M-OTs]+. Mp: 174° C. $C_{20}H_{18}INO_6S$, calculated: C, 45.55; H, 3.44; N, 2.66. Found: C, 45.53; H, 3.20; N, 2.37.

1.9. 4-cyanophenyl(4-methoxyphenyl)iodonium tosylate

White solid (45%). $^1$H NMR (DMSO-d$_6$, 300 MHz, ppm): δ 2.29 (s, 3H), 3.80 (s, 3H), 7.10 (m, 4H), 7.47 (d, 2H, J=7.8 Hz), 7.98 (d, 2H, J=8.1 Hz), 8.21 (d, 2H, J=8.7 Hz), 8.36 (d, 2H, J=8.1 Hz). $^{13}$C NMR (DMSO-d$_6$, 75 MHz, ppm): δ 20.7, 55.7, 105.5, 114.4, 117.5, 117.6, 121.1, 121.8, 125.5, 128.0, 134.8, 135.4, 137.5, 145.7, 162.3. ESI-MS: m/z=336.0 [M-OTs]+, 842.9 [2M-OTs]+. Mp: 208° C. $C_{21}H_{18}INO_4S+H_2O$, calculated: C, 48.01; H, 3.84; N, 2.67. Found: C, 47.90; H, 3.15; N, 2.34.

1.10. 4-azidophenyl(4-methoxyphenyl)iodonium tosylate

White solid (60%) $^1$H NMR (400 MHz, CD$_3$CN): 7.99-7.94 (m, 4H), 7.42 (d, 2H, 8 Hz), 7.09 (d, 2H, 8 Hz), 6.99 (d, 2H, 9.2 Hz), 6.95 (d, 2H, 9.2 Hz), 3.79 (s, 3H), 2.32 (s, 3H) $^{13}$C NMR (100 MHz, CDCl$_3$): 163.8, 145.6, 145.5, 140.0, 138.3, 137.7, 129.4, 126.6, 123.20, 118.56, 110.3, 104.9, 56.6, 21.3 ESI-MS: m/z=352.3 [M-OTs]+, 875.5 [2M-OTs]+.

1.11. 4-azidomethylphenyl(4-methoxyphenyl)iodonium tosylate

White solid (74%) $^1$H NMR (400 MHz, CD$_3$CN): 8.01-7.95 (m, 4H), 7.55 (d, 1H, 7.6 Hz), 7.46-7.43 (m, 3H), 7.09 (d, 2H, 8 Hz), 6.96 (d, 2H, 9.2 Hz), 4.40 (s, 2H), 3.80 (s, 3H), 2.31 (s, 3H) $^{13}$C NMR (100 MHz, CDCl$_3$): 163.6, 145.3, 141.0, 140.1, 138.4, 135.2, 135.1, 132.8, 132.5, 129.3, 126.5, 118.4, 116.7, 104.5, 56.5, 53.9, 21.1. ESI-MS: m/z=366.3 [M-OTs]+, 903.6 [2M-OTs]+.

1.12. 4-ethynylphenyl(4-methoxyphenyl)iodonium tosylate

White solid (64%). $^1$H NMR (400 MHz, CD$_3$CN): 7.97-7.95 (m, 4H), 7.52-7.48 (m, 4H), 7.11 (d, 2H, 7.6 Hz), 7.05 (d, 2H, 8.8 Hz), 3.82 (s, 3H), 3.61 (s, 1H), 2.32 (s, 3H) $^{13}$C NMR (100 MHz, CD$_3$CN): 160.6, 142.0, 139.4, 136.2, 134.8, 132.3, 130.0, 128.2, 122.7, 120.3, 114.3, 111.9, 81.5, 80.7, 56.3, 19.9. ESI-MS: m/z=335.3 [M-OTs]+, 841.5 [2M-OTs]+.

1.13 3-N-hydroxysuccinimidylphenyl ester(4-methoxyphenyl)iodonium tosylate)

Beige solid (36%). $^1$H NMR (400 MHz, CD$_3$CN): 2.31 (s, 3H), 2.86 (s, 4H), 3.81 (s, 3H), 6.98 (m, 2H), 7.09 (d, 2H, J=7.6 Hz), 7.42 (m, 2H), 7.61 (t, 1H, J=8.0 Hz), 8.00 (m, 2H), 8.25 (m, 1H), 8.31 (m, 1H), 8.71 (m, 1H). $^{13}$C NMR (100 MHz, CD$_3$CN): 21.2, 26.4, 56.5, 104.5, 116.7, 118.6, 126.5, 128.7, 129.3, 133.3, 134.2, 137.0, 138.7, 140.1, 141.7, 145.2, 161.3, 163.9, 170.8. ESI-MS: m/z=452.2 [M-OTs]$^+$. ≈5-10% of hydrolyzed ester were also detected.

1.14 N-hydroxysuccinimidylphenyl ester(4-methylethoxyphenyl)iodonium tosylate)

Was as white crystals (39%). $^1$H NMR (CD3CN, 300 MHz, ppm): δ 1.29 (d, 6H, J=6.0 Hz), 2.31 (s, 3H), 2.86 (s, 4H), 4.64 (m, 1H), 6.95 (m, 2H), 7.9 (d, 2H, J=7.6 Hz), 7.44 (m, 2H), 7.62, t, 1H, J=8.0 Hz), 7.97 (m, 2H), 8.27, m, 2H), 8.71 (s, 1H). $^{13}$C NMR (100 MHz, CD$_3$CN): 15.6, 21.2, 21.9, 26.5, 71.7, 103.8, 116.7, 120.0, 126.5, 128.8, 129.4, 133.4, 134.3, 137.0, 138.9, 140.1, 141.7, 145.4, 161.3, 162.5, 170.9. ESI-MS: m/z=480.2 [M-OTs]$^+$. ≈10% of hydrolyzed ester were also detected.

2. General Method for the Preparation of Iodonium Triflates 3-chloroperbenzoic acid dried in vacuo for 1 h prior to use (504 μmol) was dissolved in CH$_2$Cl$_2$ (5 mL) and the iodoarene was added (458 μmol). After 15 min of stirring at room temperature, the desired arene (anisole, 1-methylethoxybenzene or thiophene, 504 μmol) was added, the solution cooled to −20° C. and triflic acid (916 μmol) was added. The resulting dark solution was stirred at −20° C. for 15 min. After returning to room temperature, the solvent was romoved in vacuo and the residue was by flash chromatography using the appropriate gradient of CH$_2$Cl$_2$ and iPrOH. The resulting purified iodonium triflate was then crystallyzed from CH$_3$CN/Et$_2$O. Compounds described in 2.1, 2.2, 2.3, 2.4 and 2.5 were obtained using this procedure

2.1 3-N-hydroxysuccinimidylphenyl ester(4-methoxyphenyl)iodonium triflate)

Was obtained from N-hydroxysuccinimidylphenyl ester and anisole as white crystals (28%). $^1$H NMR (CD3CN, 300 MHz, ppm): δ 2.86 (s, 4H), 3.85 (s, 3H), 7.08 (d, 2H, J=6.9 Hz), 7.73 (t, 1H, J=6.0 Hz), 8.05 (d, 2H, J=6.9 Hz), 3.22-8.36 (m, 2H), 8.75 (s, 1H). $^{13}$C NMR (100 MHz, CD$_3$CN): 26.5, 56.8, 102.2, 114.8, 119.3, 129.4, 134.0, 135.0, 137.0, 139.0, 141.7, 161.2, 164.6, 170.8. ESI-MS: m/z=452.2 [M-OTf]$^+$, 1053.0 [2M-OTf]$^+$.

2.2 3-N-hydroxysuccinimidylphenyl ester(4-methylethoxyphenyl)iodonium triflate)

Was obtained from N-hydroxysuccinimidylphenyl ester and 1-methylethoxybenzene as white crystals (36%). $^1$H NMR (CD3CN, 300 MHz, ppm): δ 1.96 (m, 6H), 2.88 (s, 4H), 4.70 (m, 1H), 7.05 (m, 2H), 7.74 (t, 1H, J=8.0 Hz), 8.05 (m, 2H), 8.36 (m, 2H), 8.75 (s, 1H). ESI-MS: m/z=480.3 [M-OTf]$^+$,

2.3 3-N-hydroxysuccinimidylphenyl ester(2-thienyl)iodonium triflate

Was obtained from N-hydroxysuccinimidylphenyl ester and 1-methylethoxybenzene as white crystals (17%). $^1$H NMR (CD3CN, 300 MHz, ppm): δ 2.88 (s, 4H), 7.24 (m, 1H), 7.76 (t, 1H, J=8.0 Hz), 7.94 (m, 1H), 8.05 (m, 1H), 8.38 (m, 2H), 8.82, s, 1H). ESI-MS: m/z=428.5 [M-OTf]$^+$,

2.4 4-methyl-2-[2,2,2-trifluoro-1-allyloxy-1-(trifluoromethypethyl]phenyl-(4-methoxyphenypiodonium triflate)

Was obtained as beige crystals (56%)$^1$H NMR (400 MHz, CD$_3$CN): 2.44 (s, 3H), 3.95 (s, 3H), 4.94 (d, 2H, J=6.0 Hz), 5.57 (d, 1H, J=10, 4 Hz), 5.72 (d, 1H, J=17.2 Hz), 6.17-6.27 (m, 1H), 7.09 (d, 1H, J=8.6 Hz), 7.21 (d, 1H, J=9.0 Hz), 7.37 (m, 1H), 7.73 (s, 1H), 8.03 (d, 1H, J=9.0 Hz). ESI-MS: m/z=517.3 [M-OTf]$^+$.

2.5 4-methyl-2-[2,2,2-trifluoro-1-methoxy-1-(trifluoromethyl)ethyl]phenyl-(4-methoxyphenyl)iodonium triflate)

Was obtained as beige crystals (53%). $^1$H NMR (400 MHz, CD$_3$CN): 2.44 (s, 3H), 3.96 (s, 3H), 4.08 (s, 3H), 7.07 (d, 1H, J=8.6 Hz), 7.23 (d, 2H, J=9.2 Hz), 7.39 (d, 1H, J=8.6 Hz), 7.72 (s, 1H), 8.07 (d, 2H, J=9.2 Hz). ESI-MS: m/z=491.2 [M-OTf]$^+$.

2.6 4-maleimidophenyl-(2-thienyl)iodonium triflate

Was obtained as colorless crystals (29%). %). $^1$H NMR (400 MHz, CD$_3$CN): 6.98 (s, 2H), 7.23 (m, 1H), 7.58 (d, 2H, J=7.2 Hz), 7.92 (d, 1H, J=5.4 Hz), 8.02 (d, 1H, J=5.4 Hz), 8.16 (d, 2H, J=7.2 Hz). ESI-MS: m/z=491.2 [M-OTf]$^+$.

Example 2

Radiochemistry

[$^{125}$I] was obtained commercially from Perkin-Elmer (Shelton, Conn.) in 10$^{-5}$ M NaOH solution with a volumic acitivity of 50 μCi/μL (1.85 MBq/μL) and was diluted as desired in deionized water before use. $^{211}$At was produced using the $^{209}$Bi(α,2n)$^{211}$At reaction by bombarding a disposable internal bismuth target with α-particles from the Cyclotron Corporation CS-30 cyclotron in the National Institutes of Health Positron Emission Tomography Department. $^{211}$At was recovered from the irradiated target in acetonitrile using the dry-distillation procedure described in Lindegren, S.; Back, T.; Jensen, H. *J. Appl Rad Isot* 2001, 55, 157

Before use, the $^{211}$At solution was diluted twice in a 10 mg/mL aqueous solution of Na$_2$SO$_3$, resulting in a 1:1 ACN/water solution of NaAt.

Alternatively, $^{211}$At was produced at the Arronax facility (St Herblain, France) using an identical nuclear reaction and dry distilled using the same procedure. In this case, $^{211}$At was recovered in chloroform (CHCl$_3$), the solution evaporated to dryness under a stream of nitrogen. The dry astatine was then redissolved in an appropriate volume of 1 mg/mL or 10 mg/mL aqueous sodium sulfite before use in astatination reactions.

1.1 Reaction of Iodonium Salts with $^{125}$I

To 950 nmol of iodonium salt in 190 μL of the selected solvent equilibrated at the appropriate temperature of reaction was added 10 μL (typically 1.5 MBq) of [$^{125}$I]-NaI prepared from commercial [$^{125}$I]-NaI in 10$^{-5}$ NaOH and diluted in the appropriate amount of ultrapure water. At desired times, aliquots were withdrawn and deposited on a silica gel TLC plate and eluted with the appropriate solvent, and/or diluted in a 1/1 mixture of water/ACN and analyzed by reverse phase HPLC using the appropriate elution system. Retention indexes and elution systems used for all compounds of this study are given in ESI. Aromatic $^{125}$I species were identified by comparison of the retention index of the cold analogues.

1.2 Reaction of Iodonium Salts with $^{211}$At

To 950 nmol of iodonium salt in 180 µL of the selected solvent and equilibrated at the appropriate temperature of reaction, was added 20 µL (typically 5 MBq) of [$^{211}$At]-NaAt prepared as described above. At desired times, aliquots were withdrawn and deposited on a silica gel TLC plate and eluted with the appropriate solvent, and/or diluted in a 1/1 mixture of 0.1 N HCl/ACN. The same elution systems as in $^{125}$I procedures were used. The retention indexes of astatinated compounds were nearly identical to their iodinated analogues.

TABLE 1

RCY and selectivity for target product of the radioiodination at 90° C. and astatination at 80° C. of asymmetric iodonium tosylates in ACN-5% H$_2$O (30 min, n = 3).

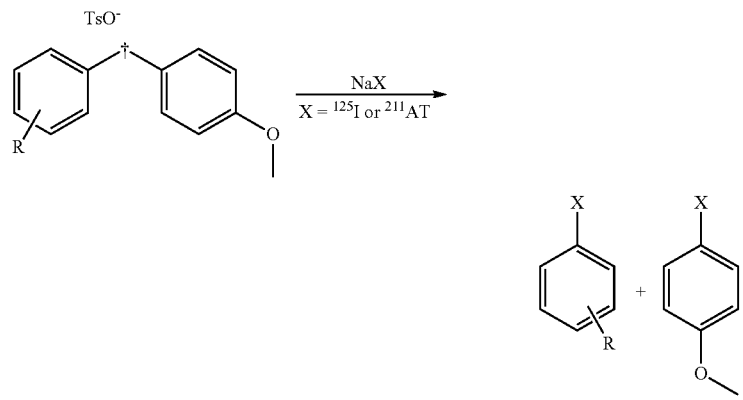

| R | $^{125}$I | | | $^{211}$At | | |
|---|---|---|---|---|---|---|
| | RCY$_{total}$$^a$ (%) | RPhI: MeOPhI ratio | ΔG$_{TS}$ (kcal/mol) exp. | RCY$_{total}$$^a$ (%) | RPhAt: MeOPhAt ratio | ΔG$_{TS}$ (kcal/mol) exp. |
| H | 61 +/− 2 | 4.8:1 | 1.13 | 97 +/− 1 | 4.2:1 | 1.04 |
| 4-Me | 43 +/− 6 | 1.5:1 | 0.29 | 97 +/− 1 | 2:1 | 0.50 |
| 3-Me | 61 +/− 1 | 4.4:1 | 1.07 | 99 +/− 1 | 3.7:1 | 0.94 |
| 2-Me | 98 +/− 1 | 27:1 | 2.38 | 98 +/− 1 | 8.1:1 | 1.51 |
| 4-Cl | 68 +/− 2 | 8:1 | 1.50 | 98 +/− 1 | 5.3:1 | 1.20 |
| 4-CO$_2$Et | 96 +/− 1 | 35:1 | 2.56 | 98 +/− 1 | 8.2:1 | 1.52 |
| 4-CN | 97 +/− 1 | >50:1 | >2.82 | 99 +/− 1 | 16:1 | 2.00 |
| 3-NO$_2$ | 82 +/− 4$^b$ | 19:1 | ND$^b$ | 99 +/− 1 | 24:1 | 2.29 |
| 4-NO$_2$ | 92 | >50:1 | >2.82 | 99 +/− 1 | 29:1 | 2.43 |
| 4-CH$_2$N$_3$ | 87$^c$ | 14:1 | | 75 | 6.5:1 | |
| 4-N$_3$ | 59$^c$ | 11:1 | | 61$^d$ | 2.5:1 | |
| 4-C≡CH | 59$^c$ | 11:1 | | 71$^c$ | 6:1 | |
| 3-CONHS | | | | 93$^d$ | 11:1 | |

$^a$Decay corrected.
$^b$Presence of 10-15% unidentified side products.
$^c$Reaction at 120° C.,
$^d$reaction at 60° C.

These results show that good yields are obtained for the iodination reaction and that high yields (superior to 70%) are obtained with the astatination reaction, independently of the substituents present on the phenyl ring

Example 3

Radiolabelling of a Biomolecule

A—Iodolabelled biomolecule

1—Preparation of [$^{125}$I]-SIB (N-succinimidyl 3-iodobenzoate) of formula (I)

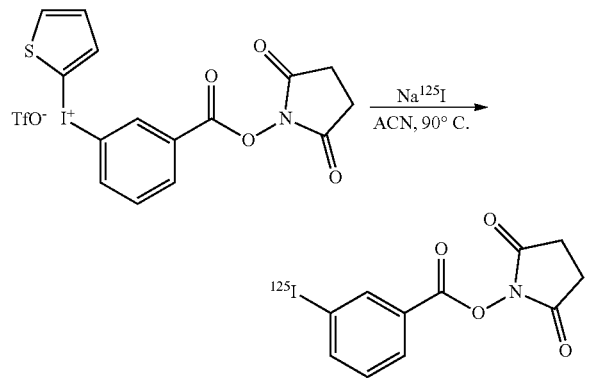

To 95 μL of 5 mM iodonium salt in ACN placed in a 1 mL glass vial was added 5 μL (50 to 500 μCi) [$^{125}$I] NaI prepared as described above. The solution was heated for 30 min at 90° C. After cooling to room temperature, an aliquot was withdrawn and analyzed by reverse phase HPLC showing the formation of [$^{125}$I]-SIB with a radiochemical yield (RCY) of 86%. The sides products were [$^{125}$I]-2-iodothiophene (2%), [$^{125}$I]-3-iodobenzoic acid (1.5%) and ≈10% of unreacted $^{125}$I$^-$ and degradation products.

Purification of [$^{125}$I]-SIB was performed as follow:

After reduction of the labeling mixture to dryness under a stream of dry nitrogen, 100 μL of Et$_2$O were added. The vial was vortexed for 30 s and the Et$_2$O was transferred to a second 1 mL vial. The Et$_2$O extraction procedure was repeated twice. An aliquote of the combined Et$_2$O layers was analyzed by HPLC, revealing the presence of 98% pure [$^{125}$I]-SIB, the remaining 2% corresponding to [$^{125}$I]-3-iodobenzoic acid. After reduction to dryness under a stream of nitrogen, the [$^{125}$I]-SIB can be reconditionned into the appropriate medium for conjugation to the chosen biomolecule/vector.

In this extraction procedure, Et$_2$O can be replaced by toluene.

[$^{125}$I]-SIB was also produced from the following iodonium precursors using identical reaction conditions.

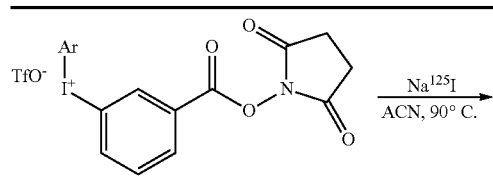

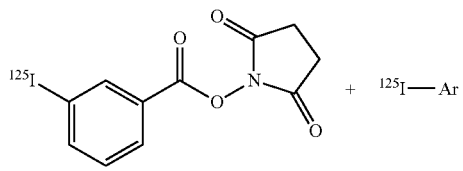

| Ar | % [$^{125}$I]-SIB | % [$^{125}$I]-3-iodobenzoic acid | % $^{125}$I-Ar |
|---|---|---|---|
| MeOPh (100° C.) | 36 | 3 | 2 |
| iPrOPh (100° C.) | 50 | 3 | 1 |
| 2-thienyl (100° C.) | 87 | 1.5 | 1 |
| 80° C. | 67 | 2 | <1 |
| 60° C. | 7 | 0 | 0 |

2-Conjugation of [$^{125}$I]-SIB to IgG 9E7.4

To [$^{125}$I]-SIB obtained as described above, placed in a 1 mL V-vial and reduced to dryness under a stream of N$_2$, was added 20 μL of DMSO. The solution was vortexed for 30 s and 100 μL of a 5.65 mg/mL of 9E7.4 IgG (anti CD138) in 0.3M borate buffer at pH 8.6 was added. After 30 min of agitation at 20° C., a chromatographic control using an ITLC-SG strip and 10% TCA as eluant indicated 75% conjugation yield. The solution was purified by gel filtration (PD10 column) using PBS as eluent, affording pure radiolabeled 9E7.4 IgG (radiochemical purity >99% as verified by ITLC-SG).

The same coupling reaction has been carried out with [$^{211}$At]-SAB, with a 75-88% conjugation yield (n=3) and preservation of the antibody immunoreactivity (85%).

3—Other Radioiodinated Compounds of Formula (I) Obtained By the Same Procedure

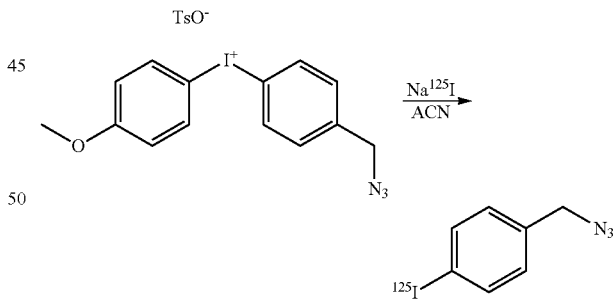

The reaction was carried out at 120° C. for 30 mn resulting in the formation of [$^{125}$I]-1-azidomethyl-4-iodobenzene (81% RCY) and [$^{125}$I]-iodoanisole (6%).

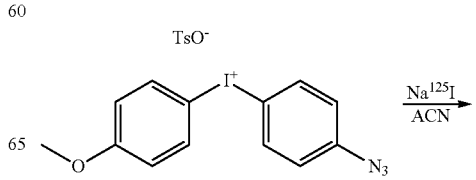

-continued

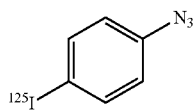

The reaction was carried out at 120° C. for 30 mn resulting in the formation of [$^{125}$I]-1-azido-4-iodobenzene (54% RCY) and [$^{125}$I]-iodoanisole (5%).

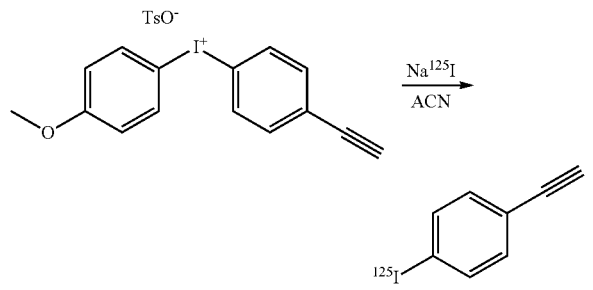

The reaction was carried out at 120° C. for 30 mn resulting in the formation of [$^{125}$I]-1-ethynyl-4-iodobenzene (54% RCY) and [$^{125}$I]-iodoanisole (5%).

4-Click Conjugation of [$^{125}$I]-1-azidomethyl-4-iodobenzene (81% RCY) with a Model tripeptide

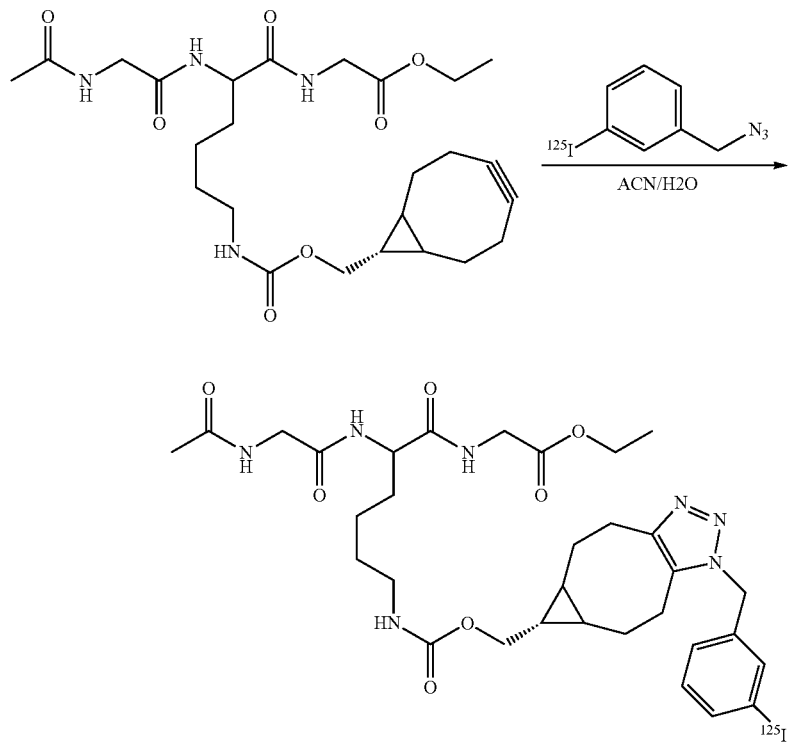

After preparation as described above, the [$^{125}$I]-1-azidomethyl-4-iodobenzene labelling solution was reduced to dryness upon which [$^{125}$I]-iodoanisole side product was eliminated by evaporation together with the solvent, resulting in an analytically pure [$^{125}$I]-1-azidomethyl-4-iodobenzene sample (HPLC) in the Et$_2$O extract. After reduction to dryness, 100⍺ of the click tripeptide (1.5 mg/mL in H$_2$O/ACN (8:2)) was added and the vial was stirred at room temperature for 3 hours. HPLC analysis showed a conjugation yield>99%.

B—Astatoarene

1—Preparation of [$^{211}$At]-SAB(N-succinimidyl 3-astatobenzoate)

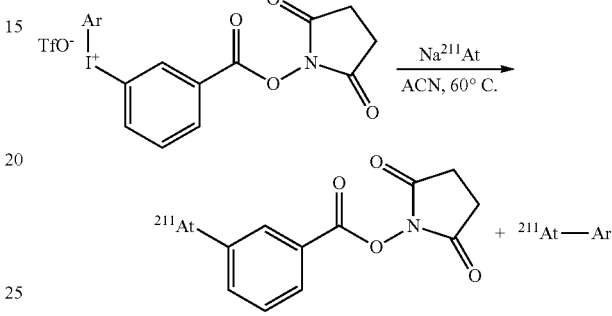

Astatine-211 was provided by the Arronax facility (St Herblain, France) in chloroform solution. Before use, it was reduced in At(–I) form by evaporation of the chloroform to dryness under a stream of nitrogen and redissolution in a 1 mg/mL sodium sulfite solution. Then, in a 1 mL vial was added 5 μL of Na$^{211}$At to 95 μL of the iodonium in ACN at a 5 mM concentration. After heating at 25° C. to 100° C. for 30 min, an aliquot was analyzed by HPLC.

| Ar | % [$^{211}$At]-SAB | % [$^{211}$At]-3-astatobenzoic acid | % $^{211}$At—Ar |
|---|---|---|---|
| MeOPh | 92 (100° C.) | <1 | 6 |
|  | 93 (60° C.) | 0 | 5 |
|  | 91 (40° C.) | 0 | 6 |
|  | 49% (25° C.) | 0 | 4 |
| iPrOPh | 85 (100° C.) | <1 | 6 |
| 2-thienyl | 79 (100° C.) | 0 | 12 |

The same extraction procedure employed for radioiodination using Et$_2$O when R=MeOPh provided [$^{211}$At]-SAB with 95% purity, with 5% 4-astatoanisole.

In particular, the above table shows the unexpected high reactivity of the $^{211}$At, even at low temperature (see for example 91% yield at 40° C. for MeOPh). In comparison, good yield are obtained with $^{125}$I above 80° C.

2—Other Astatinated Compounds Obtained by the Same Procedure

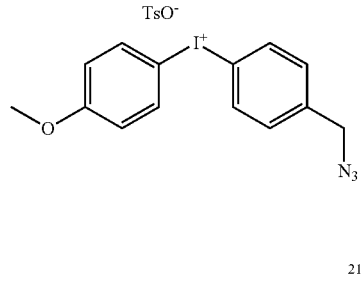

The reaction was carried out at 80° C. for 30 mn resulting in the formation of [$^{211}$At]-1-azidomethyl-4-astatobenzene (65% RCY) and [$^{211}$At]-astatoanisole (10%).

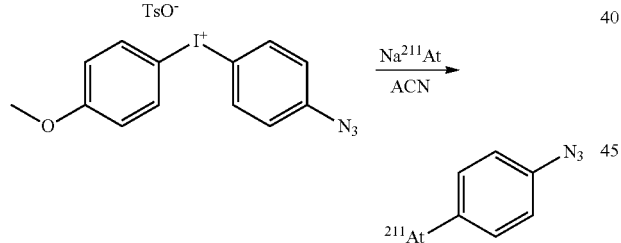

The reaction was carried out at 60° C. for 30 mn resulting in the formation of [$^{211}$At]-1-azido-4-astatobenzene (44% RCY) and [$^{211}$At]-astatoanisole (17%).

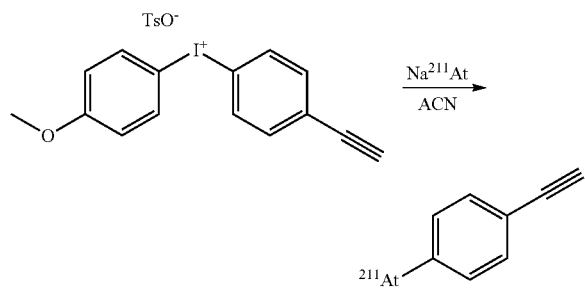

The reaction was carried out at 120° C. for 30 mn resulting in the formation of [$^{211}$At]-1-ethynyl-4-astatobenzene (66% RCY) and [$^{211}$At]-astatoanisole (11%).

Example 4

Comparison Between Iodination and Astatination

Figure 2:
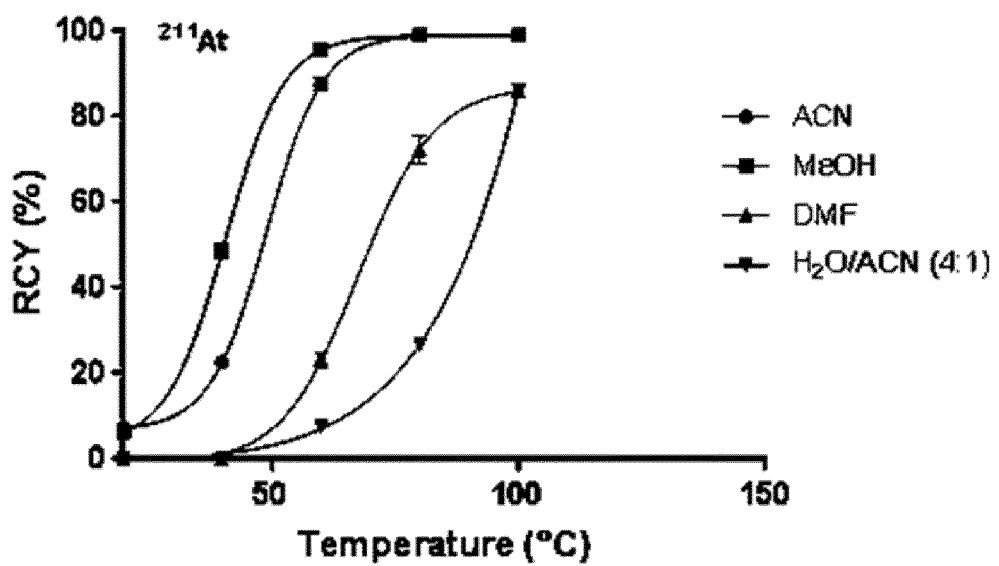
FIG. 2 shows the percentage of the radiochemical yield (RCY) of the astatination reaction depending on the solvent and temperature used.

Results of the influence of temperature and solvent study are displayed in FIGS. 1 and 2 and show a clearly distinct reactivity between iodide and astatide.

In the case of iodination, the use of ACN leads to high RCYs above 100° C., with up to 93% at 120° C.

In contrast, all solvent conditions gave RCYs superior to 80% at 100° C. or below for the astatination reaction. This shows a strong difference in terms of reactivity between the two halogens. The reactivity of astatine could not have been derived from the iodine reactivity.

Example 5

Synthesis:

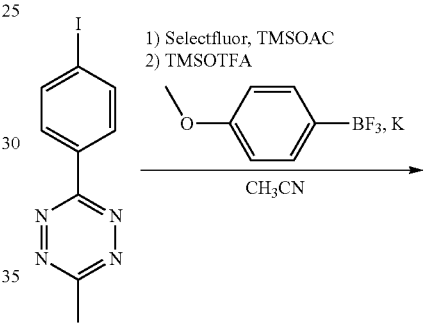

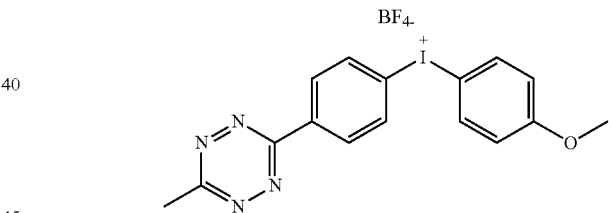

The starting 3-(p-iodophenyl)-6-methyl-1,2,4,5,tetrazine was prepared as previously reported (Angewandte, 2012, 5222-52252). The preparation of the aryliodonium salt was adapted from a previously reported procedure (Eur. J. Org. Chem. 2015, 5919-5924):

To a solution of Selectfluor (177 mg, 470 μmop in dry acetonitrile (5 mL) under argon was added TMSOAC (139 mg, 1.02 mmol) and the solution was stirred at room temperature until the solution becomes clear (≈15 min). It was then added dropwise to a solution of 3-(p-iodophenyl)-6-methyl-1,2,4,5,tetrazine (101 mg, 340 μmol) dissolved in dry acetonitrile (7.5 mL). The mixture was then stirred at room temperature for 24 h under Argon. To the solution was then added 4-methoxyphenyltrifluoroborate (84 mg, 370 μmol) and TMSOTFA (72 mg, 370 μmol) and the solution was stirred at room temperature under argon for 4 days. Volatiles were removed by rotary evaporation and the crude product was purified by flash chromatography (SiO$_2$ with CH$_2$Cl$_2$/methanol gradient) to afford a purple solid (44 mg, 28%).

NMR $^1$H (CD$_3$CN, 400 MHz, ppm): δ 3.05 (s, 3H), 3.84 (s, 3H), 7.08 (d, 2H, J=9.2 Hz), 8.06 (d, 2H, J=9.2 Hz), 8.23 (d, 2H, J=8.8 Hz), 8.59 (d, 2H, J=8.8 Hz). NMR $^{13}$C (CD$_3$CN, 100 MHz, ppm): 21.1, 56.4, 118.9, 131.4, 136.1, 136.9, 138.5, 163.5, 164.1, 168.8. NMR $^{19}$F (CD$_3$CN): −152.2. ESI-MS: m/z=405.3, [M-BF$_4$]$^+$.

Radiolabeling:

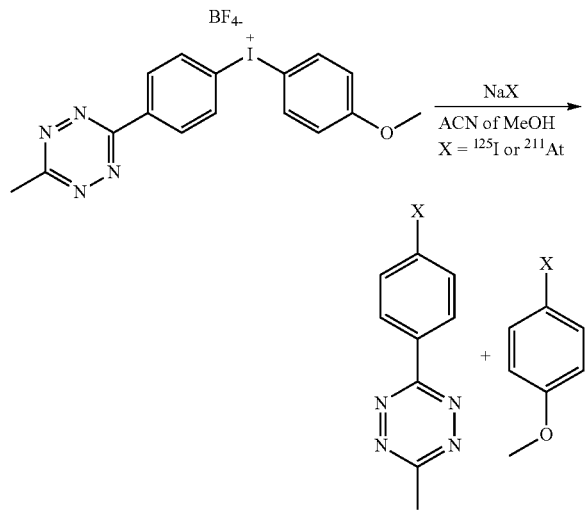

Radioiodination: To 95 μL aryliodonium salt (5 mM in ACN) was added 5 μL of Na$^{125}$I. The solution was heated at 100° C. for 15 min. An HPLC analysis indicated the formation of 96% of radioiodinated tetrazine and 2% of radioiodinated anisole. The crude solution was evaporated to dryness, dissolved in 100 μL AcOEt and purified on a normal phase silica gel cartridge (Sepak) by elution with 300 μL AcOEt, affording pure radioiodinated tetrazine (>99% radiochemical purity by HPLC).

Astatination: To 85 μL aryliodonium salt (3 mM in MeOH) was added 15 μL of Na$^{211}$At (in 1 mg/mL aqueous Na$_2$SO$_3$/MeOH 1:2) and the solution was heated at 40° C. for 30 min. An HPLC analysis indicated formation of 91% of astatinated tetrazine and 9% astatinated anisole. The crude solution was evaporated to dryness, dissolved in 100 μL AcOEt and purified on a normal phase silica gel cartridge (Sepak) by elution with 300 μL AcOEt, affording pure astatinated tetrazine (>99% radiochemical purity by HPLC).

Conjugation to Clickable Peptide:
Conjugation to BCN Peptide:

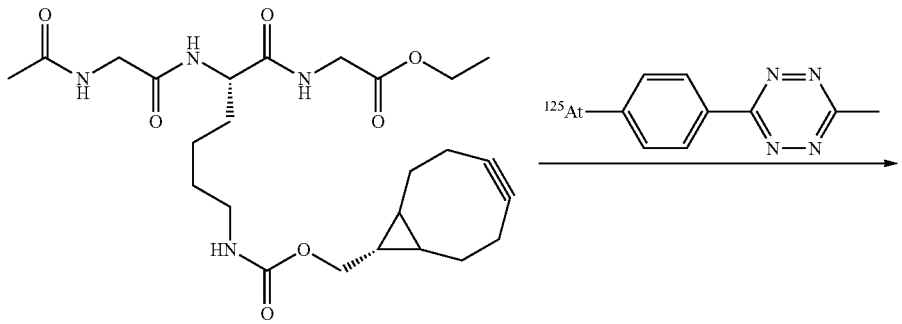

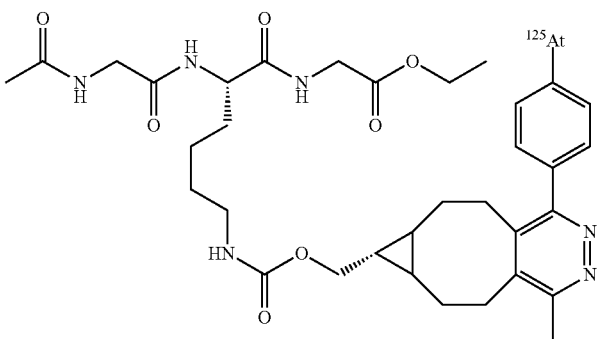

To 90 μL of BCN-peptide (100 μg/mL in 99:1 H$_2$O/MeOH) was added the astatinated tetrazine (10 μL in MeOH) and the reaction was monitored by reverse phase HPLC. Conjugation yield was 85% after 5 min and >99% after 15 min at room temperature.

Conjugation to TCO-Peptide:

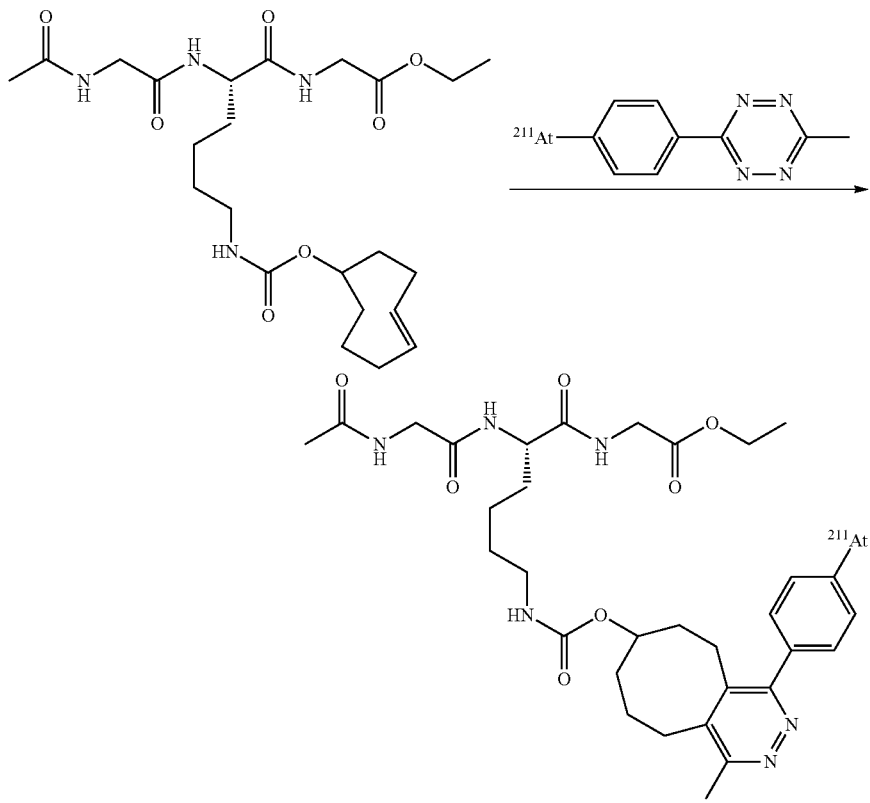

To 90 µL of TCO-peptide (100 µg/mL in 99:1 H₂O/MeOH) was added the astatinated tetrazine (10 µL in MeOH) and the reaction was monitored by reverse phase HPLC. Conjugation yield was 97% after 1 min and >99% after 15 min at room temperature.

Example 6

Synthesis:

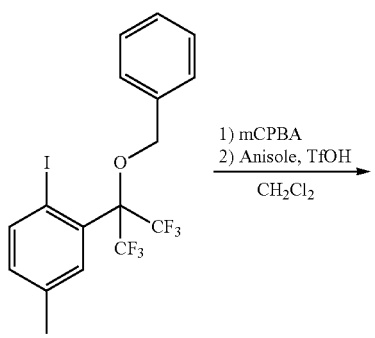

-continued

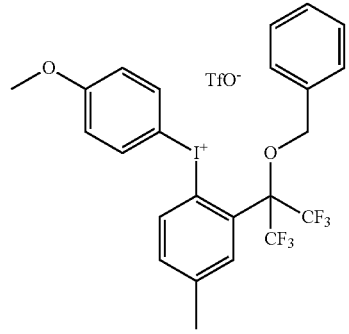

To the starting aryliodide (500 mg, 1.05 mmol) in $CH_2Cl_2$ (6 mL) was added mCPBA (260 mg, 1.16 mmol). The solution was stirred at room temperature for 30 min. Anisole (228 mg, 2.11 mmol) was then added, the solution cooled at −20° C. and triflic acid was added (317 mg, 2.11 mmol). After 40 min of stirring at −20° C., the solution was concentrated by rotary evaporation, and the crude mixture purified by flash chromatography ($SiO_2$, $CHCl_3$/MeOH gradient) affording a brown oil. To this oil was added diethylether, and after stirring at room temperature, the pure iodonium salt precipitates (67 mg, 9%).

NMR ¹H ($CD_3CN$, 400 MHz, ppm): δ 2.44 (s, 3H), 3.92 (s, 3H), 5.45 (s, 2H), 7.07 (d, 1H, J=8.6 Hz), 7.15, (d, 2H, J=9.2 Hz), 7.36, (d, 1H, J=8.6 Hz), 7.60-7.52 (m, 5H), 7.77 (s, 1H), 7.90 (d, 2H, J=9.2 Hz). ESI-MS: m/z=581.1, [M-TfO]⁺.

Radiolabeling:

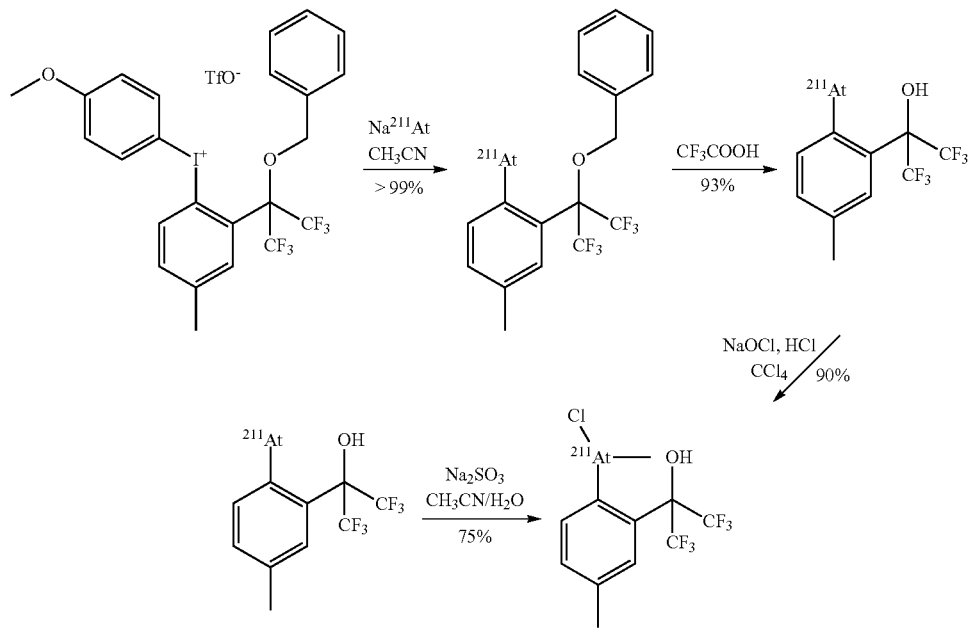

Step 1, Nucleophilic substitution: To a 1 mM solution of aryliodonium salt (285 μL in ACN), is added Na$^{211}$At (15 μL in 1 mg/mL Na$_2$SO$_3$ solution). The solution is heated at 60° C. for 10 min. HPLC analysis indicated the formation of the expected astatinated species (>99%) with no traces of asta-toanisole. The solution is evaporated under a stream of nitrogen, the residue dissolved in 100 μL CH$_2$Cl$_2$ and deposited on a Sepak silica gel cartridge. Elution with 200 μL CH$_2$Cl$_2$ afforded pure Astatinated compound (>99% radiochemical purity by HPLC).

Step 2, deprotection: The purified astatinated compound in CH$_2$Cl$_2$ solution was evaporated to dryness and 100 μL TFA were added and the mixture was agitated for about 15 min at room temperature. TFA was evaporated with a stream of nitrogen. To remove traces of remaining TFA, 100 μL of CH$_3$CN were added and evaporated with a nitrogen stream (repeated 3 times). HPLC analyses indicated that 93% of astatinated species corresponding to the expected deprotected product has formed.

Step 3, hypervalent astatine formation: The dry deprotected astatinated compound was dissolved in 100 μL CCl$_4$. 37% hydrochloric acid (2 μL) followed by NaOCl (2 μL) were then added and the reaction heated at 60° C. for 15 min. An aliquot was then analyzed by HPLC which showed conversion of 90% of starting material into the hypervalent species. To further confirm the identity of the hypervalent species, the CCl$_4$ solution was evaporated under N$_2$ stream and dissolved in 75 μL CH$_3$CN. 20 μL Na$_2$SO$_3$ solution (100 mg/mL) were added and the solution was heated for 15 min at 60° C. HPLC Analysis of an aliquot of this solution showed 75% of initial hypervalent species had revert back to the monovalent form.

Example 7

Synthesis:

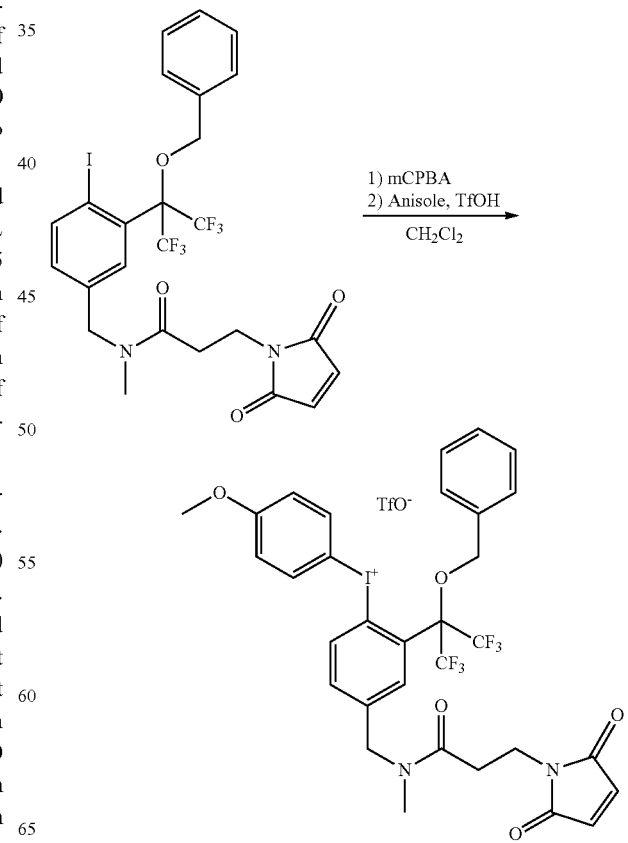

To the starting aryliodide (293 mg, 0.45 mmol) in CH$_2$Cl$_2$ (3 mL) was added mCPBA (111 mg, 0.49 mmol). The solution was stirred at room temperature for 30 min. Anisole (97 mg, 0.9 mmol) was then added, the solution cooled at −20° C. and triflic acid was added (135 mg, 0.9 mmol). After 15 min of stirring at −20° C., the solution was concentrated by rotary evaporation, and the crude mixture purified by flash chromatography (SiO$_2$, CH$_2$Cl$_2$/MeOH gradient) affording a brown oil. Crystallization in ACN/Et$_2$O provided the compound as colorless crystals (18 mg, 4%).

NMR $^1$H (CD$_3$CN, 400 MHz, ppm): δ 2.68 (t, 2H), 2.90 (s, 2H), 3.69 (t, 2H), 3.90 (s, 3H) 4.59 (s, 3H), 5.44 (s, 2H), 6.73 (s, 2H), 7.13 (m, 3H), 7.36 (m, 1H), 7.51 (m, 2H), 7.60 (m, 2H), 7.75 (s, 1H), 7.90 (m, 2H). ESI-MS: m/z=760.9.

Radiolabeling:

Step 3, hypervalent astatine formation: The dry deprotected astatinated compound was dissolved in 100 μL CCl$_4$. 37% hydrochloric acid (2 μL) followed by NaOCl (2 μL) were then added and the reaction heated at 60° C. for 30 min. An aliquot was then analyzed by HPLC which showed conversion of 93% of starting material into the hypervalent species.

The invention claimed is:

1. A method of synthesizing an astatoarene comprising reacting a diaryliodonium compound with an astatide salt, wherein the diaryliodonium compound is of formula (II):

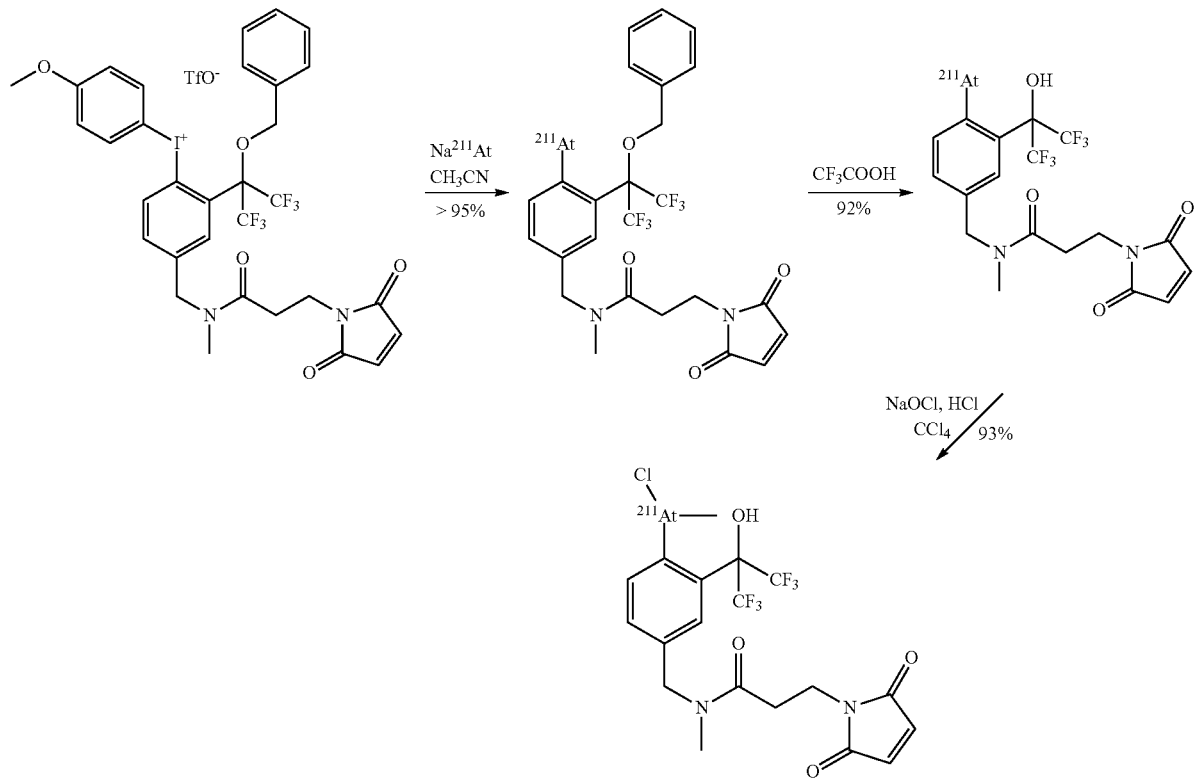

Step 1, Nucleophilic substitution: To a 1 mM solution of aryliodonium salt (285 μL in ACN), is added Na$^{211}$At (15 μL in 1 mg/mL Na$_2$SO$_3$ solution). The solution is heated at 60° C. for 10 min. HPLC analysis indicated the formation of the expected astatinated species (>95%) with no traces of astatoanisole. The solution is evaporated under a stream of nitrogen, the residue dissolved in 100 μL CH$_2$Cl$_2$ and deposited on a Sepak silica gel cartridge. Elution with 200 μL CH$_2$Cl$_2$ afforded pure Astatinated compound (>99% radiochemical purity by HPLC).

Step 2, deprotection: The purified astatinated compound in CH$_2$Cl$_2$ solution was evaporated to dryness and 100 μL TFA were added and the mixture was agitated for about 15 min at 40° C. TFA was evaporated with a stream of nitrogen. To remove traces of remaining TFA, 100 μL of CH$_3$CN were added and evaporated with a nitrogen stream (repeated 3 times). HPLC analyses indicated that 92% of astatinated species corresponding to the expected deprotected product has formed.

$$Ar_1 \overset{Y^-}{\underset{Ar_2}{I^+}} \quad (II)$$

wherein:

Ar$_1$ and Ar$_2$, independently of each other, are chosen from: (C$_6$-C$_{10}$)aryl and heteroaryl groups, said aryl and heteroaryl groups being substituted with one or several substituents selected from: (C$_1$-C$_6$)alkyl, (C$_2$-C$_6$)alkynyl, optionally substituted heteroaryl, halogen, NO$_2$, CN, N$_3$, CF$_3$, —ORa, —COORb, —C(O)R$_8$, —N=C=O, —N=C=S, —N(Ra)COORb, —(C$_1$-C$_6$)alkylene-N(Ra)—C(O)—Rb, —(C$_1$-C$_6$)alkylene-N(Ra)—C(O)—(C$_1$-C$_6$)alkylene-Rb, —(C$_1$-C$_6$)alkylene-N(Ra)—C(O)—(C$_1$-C$_6$)alkylene-C(O)O—Rb and maleimidyl, said (C$_1$-C$_6$)alkyl group being optionally substituted with one or several substituents selected from $N_3$, OH, $OCH_3$, $CF_3$, —O—$CH_2$—O—$(C_1-C_6)$alkyl, O—$(C_1-C_6)$alkenyl and —O—$(C_1-C_6)$alkylene-$(C_6-C_{10})$aryl;

Ra is H or $(C_1-C_6)$ alkyl;

Rb is selected from the group consisting of: H, $(C_1-C_6)$ alkyl, and functional groups able to bind a vector and/or a biomolecule; and Y is a monovalent anion.

2. The method according to claim 1, wherein in the diaryliodonium compound of formula (II):

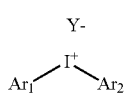
(II)

$Ar_1$ and $Ar_2$, independently of each other, are chosen from: $(C_6-C_{10})$aryl and heteroaryl groups, said aryl and heteroaryl groups being substituted with one or several substituents selected from: $(C_1-C_6)$alkyl, $(C_2-C_6)$alkynyl, optionally substituted heteroaryl, halogen, $NO_2$, CN, $N_3$, $CF_3$, —ORa, —COORb, —C(O)Ra, —N=C=O, —N=C=S, —N(Ra)COORb, —$(C_1-C_6)$alkylene-N(Ra)—C(O)—Rb, —$(C_1-C_6)$alkylene-N(Ra)—C(O)—$(C_1-C_6)$alkylene-Rb, —$(C_1-C_6)$alkylene-N(Ra)—C(O)—$(C_1-C_6)$alkylene-C(O)O—Rb and maleimidyl, said $(C_1-C_6)$alkyl group being optionally substituted with one or several substituents selected from $N_3$, OH, $OCH_3$, $CF_3$, —O—$CH_2$—O—$(C_1-C_6)$ alkyl, —O—$(C_1-C_6)$alkenyl and —O—$(C_1-C_6)$ alkylene-$(C_6-C_{10})$aryl;

Ra being H or $(C_1-C_6)$alkyl;

Rb being selected from the group consisting of: H, $(C_1-C_6)$alkyl, succinimidyl, N-hydroxysuccinimidyl, sulfosuccinimidyl, maleimidyl, biotinyl, cyclooctynyl, norbornenyl, cyclopropenyl, bicyclononynyl, and trans-cyclooctenyl; and Y is a monovalent anion.

3. The method according to claim 1, wherein the diaryliodonium compound is of formula (II-1):

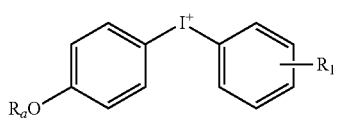
(II-1)

wherein:

$R_1$ is selected from the group consisting of: $(C_1-C_6)$alkyl, $(C_2-C_6)$alkynyl, optionally substituted heteroaryl, halogen, $NO_2$, CN, $N_3$, $CF_3$, —ORa, —COORb, —C(O)Ra, —N=C=O, —N=C=S, —N(Ra)COORb, —$(C_1-C_6)$alkylene-N(Ra)—C(O)—Rb, —$(C_1-C_6)$alkylene-N(Ra)—C(O)—$(C_1-C_6)$alkylene-Rb, —$(C_1-C_6)$alkylene-N(Ra)—C(O)—$(C_1-C_6)$alkylene-C(O)O—Rb, and maleimidyl, said $(C_1-C_6)$alkyl group being optionally substituted with one or several substituents selected from $N_3$, OH, $OCH_3$, $CF_3$ and —O—$CH_2$—CH=$CH_2$;

Ra and Rb being defined as in claim 1.

4. The method according to claim 1, wherein the astatoarene is of formula (I):

Ar—X (I)

wherein:

X is At; and

Ar is $Ar_1$ or $Ar_2$.

5. The method of claim 1, wherein the astatide salt is of formula (III):

$A^+X^-$ (III)

wherein:

X is as defined in claim 4; and

A is a monovalent cation selected among Na, K, Cs, tetraalkylammonium and tetraalkylphosphonium.

6. The method of claim 4, wherein X is radioactive.

7. The method according to claim 6, wherein X is $^{211}$At.

8. The method of claim 1, wherein the reaction is carried out in a solvent selected from the group consisting of: acetonitrile, an alcohol, dimethylformamide, water, and mixtures thereof.

9. The method of claim 1, further comprising
a purification step wherein the astatoarene is extracted by a solvent in which:
an astatide salt and the diaryliodonium salt of formula (II) are insoluble, and
said astatoarene is soluble.

10. The method of claim 1, further comprising a step of reducing astatine prior to the step of reacting.

11. A method of synthesizing an astatolabeled biomolecule and/or vector comprising the steps of:
(i) synthesizing an astatoarene according to the method of claim 1;
(ii) reacting said astatoarene with a biomolecule and/or a vector carrying a functional group reactive with said astatoarene.

12. The method according to claim 11, wherein the astatoarene is of formula (I):

Ar—X (I)

where X is radioactive.

13. The method of claim 1, wherein Y is chosen from: $CF_3COO$, TsO, MsO, NsO, TfO, $NO_3$, Br, Cl, $SO_4$ and $BF_4$.

14. The method of claim 8, wherein the alcohol is methanol.

* * * * *